United States Patent
Barraud et al.

(10) Patent No.: US 8,425,945 B2
(45) Date of Patent: Apr. 23, 2013

(54) METHODS AND COMPOSITIONS FOR REGULATING BIOFILM DEVELOPMENT

(75) Inventors: Nicolas Louis Gabriel Barraud, Coogee (AU); Jeremy Stephen Webb, Gravesend (GB); Scott Alan Rice, Glebe (AU)

(73) Assignee: NewSouth Innovations Pty Limited, Sydney (AU)

( * ) Notice: Subject to any disclaimer, the term of this patent is extended or adjusted under 35 U.S.C. 154(b) by 606 days.

(21) Appl. No.: 11/915,580
(22) PCT Filed: May 24, 2006
(86) PCT No.: PCT/AU2006/000693
§ 371 (c)(1),
(2), (4) Date: Sep. 11, 2008
(87) PCT Pub. No.: WO2006/125262
PCT Pub. Date: Nov. 30, 2006

(65) Prior Publication Data
US 2009/0214674 A1    Aug. 27, 2009

(30) Foreign Application Priority Data
May 24, 2005    (AU) ................ 2005902660

(51) Int. Cl.
*A01N 59/16*    (2006.01)
*C12Q 1/02*    (2006.01)
*A61L 2/20*    (2006.01)
*C01B 21/24*    (2006.01)
*A61K 33/26*    (2006.01)

(52) U.S. Cl.
USPC ............... 424/718; 422/4; 422/29; 423/405; 424/93.47; 424/93.51; 424/260.1; 424/647; 435/29

(58) Field of Classification Search .............. None
See application file for complete search history.

(56) References Cited

U.S. PATENT DOCUMENTS
6,610,282 B1    8/2003 Ghosh
2004/0151785 A1    8/2004 Lautt
2006/0068031 A1    3/2006 Miller et al.
2007/0154570 A1*    7/2007 Miller et al. ............. 424/718

FOREIGN PATENT DOCUMENTS
WO    WO-98/40075 A1    9/1998
WO    WO-2005/056102 A1    6/2005
WO    WO-2005/117545 A2    12/2005

OTHER PUBLICATIONS

International Preliminary Report on Patentability completed Sep. 19, 2007, for PCT Application No. PCT/AU2006/000693 filed May 24, 2006, 5 pages.

(Continued)

*Primary Examiner* — Ernst Arnold
(74) *Attorney, Agent, or Firm* — Morrison & Foerster LLP

(57) ABSTRACT

The present invention relates to methods for promoting dispersal of, or preventing formation of microbial biofilms, comprising: exposing a biofilm to an effective amount of nitric oxide or at least one nitric oxide generating or releasing agent; treating a surface or medium susceptible to biofilm formation with an effective amount of nitric oxide or at least one nitric oxide generating or releasing agent; incorporating an effective amount of nitric oxide or at least one nitric oxide generating or releasing agent in a surface or medium susceptible to biofilm formation; or inducing the accumulation of one or more reactive oxygen or nitrogen species within microorganisms within said biofilm or capable of forming a biofilm. The invention also relates to methods for maintaining or enhancing or maintaining and enhancing the functioning of a biofilm, comprising exposing a biofilm to at least one nitric oxide scavenger, at least one antioxidant or at least one nitric oxide scavenger and at least one antioxidant. The invention also relates to compositions for promoting dispersal of, or preventing formation of microbial biofilms, or for maintaining or enhancing or maintaining and enhancing the functioning of microbial biofilms.

17 Claims, 15 Drawing Sheets

OTHER PUBLICATIONS

International Search Report mailed Aug. 29, 2006, for PCT Application No. PCT/AU2006/000693 filed May 24, 2006, 2 pages.

Nablo, B. J. et al. (2005). "Inhibition of Implant-Associated Infections Via Nitric Oxide Release," *Biomaterials* 26:6984-6990.

Oh, B. K. et al. (2004). "Development and Characterization of Nitric Oxide Microsensor for Surface Nitric Oxides Measurements from NO-Releasing Sol-Gels," 56th Southeast Regional Meeting of the American Chemical Society, Nov. 10-13, 2004, Research Triangle Park, North Carolina, Abstract No. 332.

Oosterhof, J. J. H. et al. (Dec. 2003). "The Influence of Antimicrobial Peptides and Mucolytics on the Integrity of Biofilms Consisting of Bacteria and Yeasts as Affecting Voice Prosthetic Air Flow Resistances," *Biofouling* 19(6):347-353.

Schmidt, I. et al. (May 2004). "Physiologic and Proteomic Evidence for a Role of Nitric Oxide in Biofilm Formation by *Nitrosomonas europaea* and Other Ammonia Oxidizers," *Journal of Bacteriology* 186(9)12781-2788.

Schoenfisch, M. H. et al. (2004). "Nitric Oxide Release as a Means for Improving the Tissue Compatibility of in Vivo Subcutaneous Glucose Biosensors," *Book of Abstracts*, 228th ACS National Meeting, Aug. 22-26, 2004, Philadelphia, Pennsylvania, Abstract No. 159.

Barraud, N. et al. (Nov. 2006). "Involvement of Nitric Oxide in Biofilm Dispersal of *Pseudomonas aeruginosa*," *Journal of Bacteriology* 188(21):7344-7353.

Bindokas, V. P, et al. (Feb. 15, 1996). "Superoxide Production in Rat Hippocampal Neurons: Selective Imaging with Hydroethidine," *The Journal of Neuroscience* 16(4):1324-1336.

Bond, P. L. et al. (Sep. 1999). "Identification of Some of the Major Groups of Bacteria in Efficient and Nonefficient Biological Phosphorus Removal Activated Sludge Systems," *Applied and Environmental Microbiology* 65(9):4077-4084.

Brooun, A. et al. (Mar. 2000). "A Dose-Response Study of Antibiotic Resistance in *Pseudomonas aeruginosa* Biofilms," *Antimicrobial Agents and Chemotherapy* 44(3):640-646.

Crow, J. P. (Apr. 1007). "Dichlorodihydrofluorescein and Dihydrorhodamine 123 are Sensitive Indicators of Peroxynitrite in Vitro: Implications for Intracellular Measurement of Reactive Nitrogen and Oxygen Species," *Nitric Oxide* 1(2):145-157.

Davies, D. (Feb. 2003). "Understanding Biofilm Resistance to Antibacterial Agents," *Nature Reviews Drug Discovery* 2:114-122.

Dobmeier, K. P. et al. (2004). "Antibacterial Properties of Nitric Oxide-Releasing Sol-Gel Microarrays," *Biomacromolecules* 5(6):2493-2495.

Hope, C. K. et al. (2002). "Determining the Spatial Distribution of Viable and Non Viable Bacteria in Hydrated Microcosm Dental Plaques by Viability Profiling," *Journal of Applied Microbiology* 93:448-455.

Joannou, C. L. et al. (Sep. 1998). "Characterization of the Bactericidal Effects of Sodium Nitroprusside and Other Pentacyanonitrosyl Complexes on the Food Spoilage Bacterium *Clostridium sporogenes*," *Applied and Environmental Microbiology* 64(9):3195-3201.

Kelley, T. J. (1998). "Inducible Nitric Oxide Synthase Expression is Reduced in Cystic Fibrosis Murine and Human Airway Epithelial Cells," *The Journal of Clinical Investigation* 102:1200-1207.

Kelm, M. et al. (Apr. 11, 1997). "The Nitric Oxide/Superoxide Assay—Insights into the Biological Chemistry of the $NO/O_2$ Interaction," *The Journal of Biological Chemistry* 272(15):9922-9932.

Kojima, H. et al. (1999). "Fluorescent Indicators for Imaging Nitric Oxide Production," *Angewandte Chemie International Edition* 38(21):3209-3212.

Mai-Prochnow, A. et al. (Jun. 2004). "Biofilm Development and Cell Death in the Marine Bacterium *Pseudoalteromonas tunicate*," *Applied and Environmental Microbiology* 70(6):3232-3238.

Meyer, R. L. et al. (2003). "Microscale Structure and Function of Anaerobic-Aerobic Granules Containing Glycogen Accumulating Organisms," *FEMS Microbiology Ecology* 45:253-261.

Moller, S. et al. (Feb. 1998). "In Situ Gene Expression in Mixed-Culture Biofilms: Evidence of Metabolic Interactions Between Community Members," *Applied and Environmental Microbiology* 64(2):721-732.

Sauer, K. et al. (Feb. 2002). "*Pseudomonas aeruginosa* Displays Multiple Phenotypes During Development as a Biofilm," *Journal of Bacteriology* 184(4):1140-1154.

Smith, J. N. et al. (2001). "Mechanisms of Nitric Oxide Release from Nitrovasodilators in Aqueous Solution: Reaction of the Nitroprusside Ion ($[Fe(CN)5NO]^{2-}$) with L-Ascorbic Acid," *Journal of Inorganic Biochemistry* 87:165-173.

Storey, M. V. et al. (2001), "Persistence of Two Model Enteric Viruses (B40-8 and MS-2 Bacteriophages) in Water Distribution Pipe Biofilms," *Water Sciences and Technology* 43(12):133-138.

Supplementary European Search Report and Search Opinion mailed Oct. 29, 2008, for EP Application No. 06741113.2 filed May 24, 2006, 13 pages.

Webb, J. S. et al. (Aug. 2003). "Cell Death in *Pseudomonas aeruginosa* Biofilm Development," *Journal of Bacteriology* 185(15):4585-4592.

Carlsson, S. (2005). *Antibacterial Effects of Nitrite in Urine*. Karolinska Institutet: Stockholm, Sweden, 59 pages.

Carlsson, S. (Jun. 2005). "Intravesical Nitric Oxide Delivery for Prevention of Catheter-Associated Urinary Tract Infections," *Antimicrobial Agents and Chemotherapy* 49(6):2352-2355.

Nablo, B. and Schoenfisch, M. (2003). "Antibacterial Properties of nitric Oxide-Releasing Sol-Gels," *Journal of Biomedical Materials Research* 67A:1276-1283.

Singapore Written Opinion mailed Feb. 5, 2009, for Application No. 200718059-9 filed May 24, 2006, 8 pages.

Stewart, P. S. et al. (Feb. 2000). "Effect of Catalase on Hydrogen Peroxide Penetration into *Pseudomonas aeruginosa* Biofilms," *Applied and Enviromental Microbiology* 66(2):836-838.

Third Party Written Opinion mailed to the Canadian Intellectual Property Office on Mar. 24, 2009, for Canadian Patent Application No. 2609378 filed Nov. 23, 2007, 2 pages.

Nablo et al., "Nitric Oxide-Releasing Sol-Gels as Antibacterial Coatings for Orthopedic Implants", Biomaterials, vol. 26, 2005, pp. 917-924.

* cited by examiner

A

B

**Effect of SNP on Dispersal of *Vibrio cholerae* Biofilms**

Figure 12

**Effect of SNAP on Dispersal of *Vibrio cholerae* Biofilms**

Figure 13

Effect of SNP on Dispersal of *Eschericia coli* Biofilms

Effect of SNP on Dispersal of *Bacillus licheniformis* Biofilms

Effect of SNP on Dispersal of *Candida albicans* Biofilms

Effect of SNP on Dispersal of *Staphylococcus epidermidis* Biofilms

METHODS AND COMPOSITIONS FOR REGULATING BIOFILM DEVELOPMENT

FIELD OF THE INVENTION

The present invention relates to methods and compositions for regulating programmed cell death in microorganisms and for promoting or inhibiting dispersal of microorganisms from biofilms.

BACKGROUND OF THE INVENTION

Biofilms are three dimensional microbial growth forms comprising bacterial communities and the extracellular matrix they produce. Biofilms are ubiquitous in the environment and may form on solid surfaces where water is available or in suspension, for example as flocs or granules. Biofilms cause significant industrial damage, causing, for example, fouling and corrosion in fluid processes such as water distribution and treatment systems, pulp and paper manufacturing systems, heat exchange systems and cooling towers, and contributing to the souring of oil in pipelines and reservoirs. From a public health perspective, biofilms are also important reservoirs of pathogens in water systems such as drinking water, reservoirs and pipes. Biofilms are also associated with a number of chronic infections in humans, for example otitis media (biofilms on surfaces of the ear), bacterial endocarditis (biofilms on surfaces of the heart and heart valves), cystic fibrosis (biofilms on surfaces of the lungs) and kidney stones, and readily form on medical equipment such as implantable medical devices.

However notwithstanding the significant detrimental effects of biofilms in many environments, biofilms may also be of benefit. For example, in waste water treatment systems suspended floc biofilms or surface-associated biofilms on membranes are said to facilitate nutrient removal, such as in denitrification.

Accordingly, there is a clear need both for effective strategies to eliminate deleterious biofilms and to enhance the activity of beneficial biofilms.

Biofilms are essentially multicellular microbial communities, the formation and development of which is dependent on various multicellular traits of the member organisms, such as cell-cell signalling. Extracellular signalling systems such as quorum sensing are used by bacteria to assess cell density and initiate changes in gene expression and phenotypes when sufficient concentrations of signalling molecules are reached. This is associated with differential gene expression, leading to the induction of, for example, virulence factors and/or defence mechanisms, and with cell differentiation such that biofilm-associated cells become highly differentiated from free-living (planktonic) cells.

As the cells within biofilms differentiate and biofilms mature, reduced metabolic rates, the cellular expression of defence mechanisms and the reduced ability of antimicrobial agents to penetrate the biofilm results in increased antimicrobial resistance and make biofilms particularly difficult to eradicate. Present biofilm control strategies typically target the early stages of biofilm development and involve the use of toxic antimicrobial agents. However such toxic agents present their own downstream problems due to their release into the environment. Improved strategies for biofilm control are clearly required.

It has recently been discovered that *Pseudomonas aeruginosa* cells within biofilms undergo programmed cell death and lysis in the normal course of the biofilm lifecycle (Webb et al, 2003, Cell death in *Pseudomonas aeruginosa* biofilm development, *J. Bact.*, 185: 4585-4592). It is believed that programmed cell death in biofilms of *P. aeruginosa* is prophage-mediated and plays a role in facilitating differentiation and dispersal of a subpopulation of surviving cells from the biofilm.

The present invention is based on the inventors' finding that this phenomenon of programmed cell death in biofilms is linked to the accumulation of reactive oxygen and nitrogen species (RONS) within organisms of the biofilm and that the process of programmed cell death, and dispersal of cells from a biofilm into planktonic cells, can be induced using nitric oxide generators. The ability to increase nitric oxide concentrations in vivo enables the regulation and manipulation of biofilm developmental processes, by promoting programmed cell death, and increases the sensitivity of the cells to antimicrobial agents, thereby providing avenues for inhibiting and/or reversing biofilm development.

SUMMARY OF THE INVENTION

The present invention relates to a method for promoting dispersal of microorganisms from a biofilm, the method comprising exposing the biofilm to an effective amount of nitric oxide or at least one nitric oxide generating or releasing agent.

The present invention also relates to a method for promoting dispersal of microorganisms from a biofilm, the method comprising inducing the accumulation of one or more reactive oxygen and nitrogen species within the microorganisms.

The present invention also relates to a method for inhibiting biofilm formation and/or development, the method comprising treating a surface or other medium susceptible to biofilm formation an effective amount of nitric oxide or at least one nitric oxide generating or releasing agent.

Thus, according to a first aspect of the present invention, there is provided a method for promoting dispersal of, or preventing formation of a microbial biofilm, the method comprising:

exposing said biofilm to an effective amount of nitric oxide or at least one nitric oxide generating or releasing agent;

treating a surface or medium susceptible to biofilm formation with an effective amount of nitric oxide or at least one nitric oxide generating or releasing agent;

incorporating an effective amount of nitric oxide or at least one nitric oxide generating or releasing agent in a surface or medium susceptible to biofilm formation; or inducing the accumulation of one or more reactive oxygen or nitrogen species within microorganisms within said biofilm or capable of forming a biofilm.

The at least one nitric oxide generating or releasing agent may comprise one or more nitric oxide donors. Said one or more nitric oxide donors may be selected from sodium nitroprusside, S-nitroso-L-glutathione, S-nitroso-N-acetylpenicillamine or a combination thereof.

Typically the nitric oxide donor is provided in a non-toxic concentration. For example, the concentration may be in the nanomolar, micromolar or millimolar range, such as from about 1 nM to about 10 mM or from about 10 nM to about 5 µM.

The biofilm may be surface-associated or suspended. The suspended biofilm may be in the form of flocs or granules.

The microorganisms present in the biofilms or capable of forming biofilms may be of a single species or of multiple species.

The microorganisms within said biofilm or capable of forming a biofilm may comprise bacterial or fungal species or both, and may comprise one or more species selected from, for example, *Candida* spp., *Hormoconis* spp., *Pseudomonas* spp., *Pseudoalteromonas* spp., *Staphylococcus* spp., *Streptococcus* spp., *Shigella* spp., *Mycobacterium* spp., *Enterococcus* spp., *Escherichia* spp., *Salmonella* spp., *Legionella* spp., *Haemophilus* spp., *Bacillus* spp., *Desulfovibrio* spp., *Shewanella* spp., *Geobacter* spp., *Klebsiella* spp., *Proteus* spp., *Aeromonas* spp., *Arthrobacter* spp., *Micrococcus* spp., *Serratia* spp., *Porphyromonas* spp., *Fusobacterium* spp. and *Vibrio* spp., representative examples of such species being *Candida albicans, P. aeruginosa, Staphylococcus epidermidis, Escherichia coli, Bacillus licheniformis, Serratia marcescens, Fusobacterium nucleatum*, and *Vibrio Cholerae*.

The method may further comprise treating the surface or medium with, incorporating in said surface or medium, or exposing the microorganisms within said biofilm or capable of forming a biofilm to, at least one antimicrobial agent. By way of example, the antibiotic may be an aminoglycoside such as tobramycin, the surfactant may be sodium dodecyl sulfate and the oxidative stress-inducing agent may be hydrogen peroxide, hypochlorous acid, chlorine or chloramine.

Reactive oxygen and nitrogen species which may accumulate in microorganisms of a biofilm or capable of forming biofilms treated by a method of the invention may include peroxynitrite, nitric oxide, hydrogen peroxide and superoxide radicals.

In one embodiment the reactive oxygen and nitrogen species is peroxynitrite.

Accumulation of reactive oxygen and nitrogen species may be achieved by exposing the biofilm to an effective amount of nitric oxide or at least one nitric oxide generating or releasing agent.

Methods of the invention for promoting dispersal of or preventing formation of biofilms may comprise inducing differentiation events in microorganisms within said biofilm which lead to dispersal or may comprise preventing induction of differentiation events in microorganisms which lead to biofilm formation. Alternatively, or as well, methods of the invention may comprise increasing the sensitivity of a microorganism to antimicrobial agents.

The present invention also relates to a method for the treatment and/or prevention of a condition associated with biofilm development, comprising administering to a subject an effective amount of nitric oxide or at least one nitric oxide generating or releasing agent.

Thus, a method of the invention for promoting dispersal of or preventing formation of biofilms may comprise administering to a subject an effective amount of nitric oxide or at least one nitric oxide generating or releasing agent for the treatment or prevention of a biofilm-associated condition in said subject, optionally together with at least one antimicrobial agent.

The agent and/or the antimicrobial agent may be coated onto or be impregnated in or incorporated in the surface of a suitable medical device such as a catheter, stent, prosthesis or other surgical or implantable device.

The present invention also relates to compositions for promoting dispersal of microorganisms from a biofilm, or for inhibiting biofilm formation and/or development.

Thus, according to another aspect of the invention, there is provided a composition for promoting dispersal of, or preventing formation of a microbial biofilm, the composition comprising nitric oxide, at least one nitric oxide generating or releasing agent or nitric oxide and a nitric oxide generating or releasing agent, together with a suitable carrier.

The at least one nitric oxide generating or releasing agent may comprise one or more nitric oxide donors. Said one or more nitric oxide donors may be selected from sodium nitroprusside, S-nitroso-L-glutathione, S-nitroso-N-acetylpenicillamine or a combination thereof.

In one embodiment the nitric oxide donor is sodium nitroprusside.

In particular embodiments the composition may be an antifouling composition, a medical device or component thereof, a coating for a medical device or a pharmaceutical composition.

The composition may further comprise at least one antimicrobial agent. The antimicrobial agent may be any antimicrobial agent such as an antibiotic, a surfactant or oxidative stress-inducing agent. By way of example, the antibiotic may be an aminoglycoside such as tobramycin, the surfactant may be sodium dodecyl sulfate and the oxidative stress-inducing agent may be hydrogen peroxide, hypochlorous acid, chlorine or chloramine.

A composition of the invention for promoting dispersal of, or preventing formation of a microbial biofilm, may: induce differentiation events in microorganisms within said biofilm which lead to dispersal or prevent induction of differentiation events in microorganisms which lead to biofilm formation; increase the sensitivity of said microorganisms to antimicrobial agents; or may provide a combination of these effects.

The present invention also relates to compositions for treating and/or preventing a condition associated with biofilm development.

Thus, a composition of the invention for promoting dispersal of, or preventing formation of a microbial biofilm may be suitable for treating or preventing a biofilm-associated condition of a subject, and may optionally comprise at least one antimicrobial agent.

The present invention also relates to methods for maintaining and/or enhancing the functioning of a biofilm, comprising exposing the biofilm to at least one nitric oxide scavenger and/or at least one antioxidant.

Thus, according to another aspect of the invention, there is provided a method for maintaining or enhancing the functioning of a biofilm, the method comprising exposing the biofilm to at least one nitric oxide scavenger, at least one antioxidant or at least one nitric oxide scavenger and at least one antioxidant.

In one embodiment, the nitric oxide scavenger is 2-phenyl-4,4,5,5-tetramethyl-imidazoline-1-oxyl 3-oxide.

The antioxidant may be selected from the group consisting of: thioredoxin, superoxide dismutase, glutathione and ascorbic acid.

The method may comprise inhibiting differentiation events in microorganisms within said biofilm which lead to dispersal.

According to another aspect of the present invention there is provided a composition for maintaining or enhancing, or maintaining and enhancing the functioning of a biofilm, the composition comprising at least one nitric oxide scavenger and/or at least one antioxidant together with a suitable carrier.

The composition may inhibit differentiation events in microorganisms within said biofilm which lead to dispersal.

DEFINITIONS

As used herein the term "biofilm" refers to any three-dimensional, matrix-encased microbial community displaying multicellular characteristics. Accordingly, as used herein, the term biofilm includes surface-associated biofilms as well as biofilms in suspension, such as flocs and granules. Biofilms may comprise a single microbial species or may be mixed species complexes, and may include bacteria as well as fungi, algae, protozoa, or other microorganisms.

As used herein the term "surface" includes both biological surfaces and non-biological surfaces. Biological surfaces typically include surfaces both internal (such as tissues and membranes) and external (such as skin, seeds, plant foliage) to an organism, including bacterial membranes and cell walls, Biological surfaces also include other natural surfaces such as wood or fibre. A non-biological surface may be any man made surface of any composition that supports the establishment and development of a biofilm. Such surfaces may be present in industrial plants and equipment. Further, for the purposes of the present invention, a surface may be porous (such as a membrane) or non-porous, rigid or flexible.

As used herein the term "dispersal" as it relates to a biofilm means the process of detachment of cells from surfaces, including other cells (such as, one another, biofilm(s)), and a return to a planktonic phenotype or behaviour of those cells.

As used herein the term "programmed cell death" means a developmental event within a biofilm that occurs at defined stages and causes autolysis, cellular differentiation and the development of subpopulations of cells with specific phenotypes.

As used herein the term "exposing" means administering to, or otherwise bringing into contact with. A microorganism or biofilm may be exposed to an active agent directly or indirectly. Typically direct exposure refers to administration of the agent to the microorganism or biofilm to be treated or otherwise bringing the microorganism or biofilm into contact with the agent itself. Typically indirect exposure refers to the administration of a precursor of the active agent or a compound or molecule capable of generating, either solely or in reaction with other compounds or molecules, the active agent to the microorganism or biofilm or otherwise bringing the microorganism or biofilm into contact therewith. Similarly, the terms "treat" and "treating" and variations thereof as used herein mean administering to, or otherwise bringing into contact with.

As used herein the term "effective amount" includes within its meaning a non-toxic but sufficient amount or concentration of an agent to provide the desired effect. The exact amount/concentration required will vary depending on factors such as the species of microorganism(s) being treated, the extent, severity and/or age of a biofilm being treated, whether the biofilm is surface-associated or suspended, the particular agent(s) being administered and the mode of administration and so forth. Thus, it is not possible to specify an exact "effective amount". However, for any given case, an appropriate "effective amount" may be determined by one of ordinary skill in the art using only routine experimentation.

As used herein the term "non-toxic" as it pertains to concentrations or amounts of a substance means concentrations or amounts of a substance which do not have a direct toxic effect on cells, do not kill individually free-living cells, but which may operate as a signal that triggers induction of differentiation processes in biofilms, which involve a programmed cell death response and which therefore may result in death of a subpopulation of cells, generation of dispersal cells and the dispersal of biofilms. For example, with reference to nitric oxide donors, a non-toxic concentration or amount may comprise 100 mM nitric oxide donor, or less.

As used herein the term "functioning" as it pertains to a biofilm may be measured with reference to any one or more of the following parameters: the viability of the microorganisms in the biofilm, the activity(ies) of the microorganisms in the biofilm, the density of the microorganisms in the biofilm, the lifespan of the biofilm and the efficacy of the biofilm in performing a specific function, such as in the case of biofilms in wastewater systems, the removal of nutrients. Accordingly, in the context of the present invention "maintaining" biofilm functioning means preventing or at least substantially reducing the developmental processes of programmed cell death and dispersal such that microorganism viability, microorganism activity, biofilm lifespan and or biofilm function is not significantly reduced. "Enhancing" biofilm functioning means increasing or improving any one or more of the above parameters in comparison to a biofilm not treated in accordance with the present invention.

As used herein the term "inhibiting" as it pertains to biofilms means complete or partial inhibition of biofilm formation and/or development and also includes within its scope the reversal of biofilm development or processes associated with biofilm formation and/or development. Further, inhibition may be permanent or temporary. In terms of temporary inhibition, biofilm formation and/or development may be inhibited for a time sufficient to produce the desired effect.

In the context of this specification, the term "comprising" means "including principally, but not necessarily solely". Furthermore, variations of the word "comprising", such as "comprise" and "comprises", have correspondingly varied meanings.

BRIEF DESCRIPTION OF THE DRAWINGS

The present invention will now be described, by way of example only, with reference to the following drawings.

FIG. 12. Effect of SNP on dispersal of *Vibrio cholerae* biofilms.

FIG. 13. Effect of SNAP on dispersal of *Vibrio cholerae* biofilms.

DETAILED DESCRIPTION OF THE INVENTION

Figure 1:
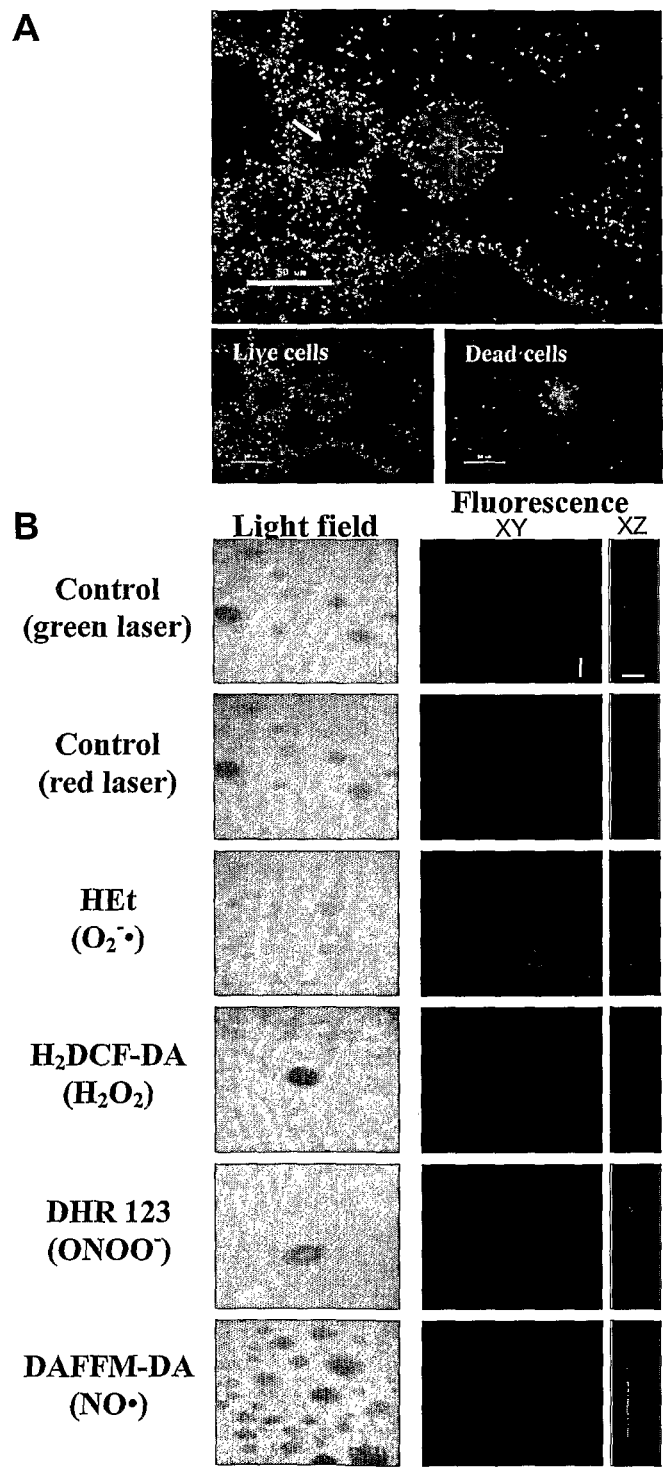
FIG. 1. Cell death and dispersal events in *P. aeruginosa* biofilms correlate with the accumulation of reactive oxygen and nitrogen species within microcolony structures. (A) Confocal micrograph showing a 7 day biofilm stained with the BacLight LIVE/DEAD stain (micrographs for live and dead cells are also shown independently in separate panels). White arrow indicates a hollow structure within a biofilm. Black arrow indicates dead cells within a biofilm. Bar, 50 µm. (B) Confocal micrographs of microcolonies in a 7 day biofilm, Biofilms were stained with fluorescent dyes detecting specific RONS. Left panel are phase contrast images, right panel are fluorescence images showing RONS accumulation in XY (top down) and XZ (side-on) views. Bars, 50 µm. Images are representative of at least 3 independent experiments.

*P. aeruginosa* is a ubiquitous soil- and water-borne opportunistic pathogen that readily forms both single species and multi-species biofilms. *P. aeruginosa* has also become a model organism for studying biofilm formation and development. Recent studies of *P. aeruginosa* biofilms have identified dispersal of cells from the interior portions of microcolonies, and programmed cell death of cells which can result in detachment and sloughing events (Sauer et al., 2002, *Pseudomonas aeruginosa* displays multiple phenotypes during development as a biofilm, *J. Bact.*, 184: 1140-1154; Webb et al., 2003, Cell death in *Pseudomonas aeruginosa* biofilm development, *J. Bact*, 185: 4585-4592). Subsequently, programmed cell death has been reported in other model biofilm forming bacteria (Mai-Prochnow et al., 2004, Biofilm development and cell death in the marine bacterium *Pseudoalteromonas tunicata*, *Appl. Environ. Microbiol.* 70: 3232-3238), in mixed species oral biofilms (Hope et al., 2002, Determining the spatial distribution of viable and non viable bacteria in hydrated microcosm dental plaques by viability profiling, *J. Appl. Microbiol.*, 1993: 448-455) and in mixed species granular biofilms in waste water treatment processes (Meyer et al., 2003, Microscale structure and function of anaerobic-aerobic granules containing glycogen accumulating organisms, *FEMS Microbiol. Ecol.*, 45: 253-261), thereby suggesting that programmed cell death is a general feature of bacterial biofilm development. The exploitation, either by way of enhancement or inhibition, of the mechanisms that trigger cell death and detachment in biofilm cells will lead to novel technologies for the manipulation of biofilms in a broad range of medical, industrial and bioprocessing situations.

Utilising fluorescent dye-based systems for the detection and analysis of reactive oxygen and nitrogen species (RONS) in biofilms, the present inventors have found that the RONS peroxynitrite (ONOO—) accumulates in *P. aeruginosa* biofilms.

Peroxynitrite is a potent oxidant with a wide range of biological effects. It is capable of reacting with a number of other biomolecules and causing cellular damage. An immediate precursor of peroxynitrite is nitric oxide, a widespread intercellular and intracellular signalling molecule in biological systems. Nitric oxide rapidly reacts with a number of compounds, including oxygen-derived radicals. In one such reaction nitric oxide readily reacts with superoxide to yield the peroxynitrite:

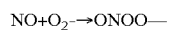

NO+$O_2^-$→ONOO—

The inventors have found that treatment of biofilms with low non-toxic concentrations of a nitric oxide donor compound induces programmed cell death and dispersal of cells from the biofilm, leading to an increase in the ratio of planktonic to biofilm cells and a reduction in surface coverage of the biofilm. Thus, disclosed herein for the first time is evidence that low, non-toxic concentrations of nitric oxide can be used to manipulate the behavioural processes of biofilm cells. In contrast, higher, toxic concentrations of nitric oxide do not achieve the dispersal of cells from biofilms, but rather promote biofilm growth.

Accordingly, one aspect of the present invention relates to a method for promoting dispersal of microorganisms from a biofilm, the method comprising exposing the biofilm to an effective amount of nitric oxide or at least one nitric oxide generating or releasing agent. The invention also relates to methods for inducing programmed cell death in a microorganism wherein the microorganism is exposed to an effective amount of nitric oxide or at least one nitric oxide generating or releasing agent, and to methods for inhibiting biofilm formation and/or development wherein a surface susceptible to biofilm formation is treated with an effective amount of nitric oxide or at least one nitric oxide generating or releasing agent.

The present inventors have also found that treatment with a nitric oxide donor increases susceptibility of both biofilm and planktonic cells to various antimicrobial agents. Accordingly, the present invention also provides methods and compositions for increasing the susceptibility of microorganisms to antimicrobial agents.

The person skilled in the art will appreciate that nitric oxide may be used directly to achieve the desired effect, or alternatively any agent capable of generating or releasing nitric oxide, may be used. The agent may generate or release nitric oxide external to the organisms to be treated, or more typically in vivo. Methods of the invention are exemplified herein using nitric oxide donors such as sodium nitroprusside, but those skilled in the art will appreciate that the invention is not so limited.

Examples of nitric oxide donors suitable for use in accordance with the present invention include, but are not limited to sodium nitroprusside (SNP), S-nitroso-L-glutathione (GSNO), GSNO monoethyl ester, S-nitroso-N-acetylpenicillamine (SNAP), glyco-SNAP, L-arginine, N,N'-dinitroso-N,N'-dimethylphenylenediamine (BNN3), N,N'-dinitrosophenylenediamine-N,N'-diacetic acid (BNN5), BNN5-Na, BNN5 methyl ester, 2-hydroxybenzoic acid 3-nitrooxymethylphenyl ester (B-NOD), dephostatin, 3,4-dephostatin, diethylamine NONOate, diethylamine NONOate/AM, S,S'-dinitrosodithiol, S-nitrosocaptopril, $N^G$-hydroxy-L-arginine monoacetate salt, Angeli's salt, 1-hydroxy-2-oxo-3-(3-aminopropyl)-3-isopropyl-1-triazene (NOC-5), 1-hydroxy-2-oxo-3-(N-3-methyl-aminopropyl)-3-methyl-1-triazene (NOC-7), 6-(2-hydroxy-1-methyl-2-nitrisohydrazino)-N-methyl-1-hyxanamine (NOC-9), 1-hydroxy-2-oxo-3-(N-ethyl-2-aminoethyl)-3-ethyl-1-triazene (NOC-12), 2,2'-(hydroxynitrosohydrazono)bis-ethanamine (NOC-18), (±)-(E)-Methyl-2-[(E)-hydroxyimino]-5-nitro-6-methoxy-3-hexeneamide (NOR-1), (±)-(E)-4-ethyl-2-[(E)-hydroxyimino]-5-nitro-3-hexenamide (NOR-3), (±)-N-[(E)-4-ethyl-2-[(Z)-hydroxyimino]-5-nitro-3-hexene-1-yl]-3-pyridine carboxamide (NOR-4), 4-phenyl-3-furoxancarbonitrile, PROLI/NO (L-proline in methanolic sodium methoxide), 3-morphorlinosydnonimine (SIN-1), S-nitroso-N-valerylpenicillamine (SNVP), spermine NONOate, ethyl nitrite and streptozotocin.

In general, nitric oxide donors, including S-nitroso, O-nitroso, C-nitroso and N-nitroso compounds and nitro derivatives thereof and metal NO complexes, but not excluding other NO generating compounds, useful for the purposes of the present invention may be found in "Methods in Nitric Oxide Research," edited by Feelisch, M., and Stamler, J. S., John Wiley & Sons, New York, 1996, pages 71-115, the disclosure of which is incorporated herein by reference. A range of additional nitric oxide donors are known to those skilled in the art and the present invention is not limited by the identity of the particular donor(s) used. Indeed the selection of the appropriate donor for a particular application of the invention may be made on a case-by-case basis.

Nitric oxide generating or releasing agents are typically used at low, non-toxic concentrations. The concentration may be nanomolar, micromolar, or millimolar. In particular embodiments, the concentration may be between about 1 nM and about 100 mM, between about 10 nM and about 50 mM, between about 25 nM and about 50 mM, between about 50 nM and about 25 mM, between about 100 nM and about 10 mM, between about 200 nM and about 1 mM, between about 1 nM and about 10 mM, between about 10 nM and 50 µM, between about 10 nM and 25 µM, between about 10 nM and 10 µM, between about 10 nM and 5 µM, between about 10 nM and 1 µM, or between about 10 nM and 500 nM. The most suitable concentration to achieve the desired effect will depend on a number of factors and may be determined by those skilled in the art using routine experimentation. Such factors include, but are not limited to, the particular agent(s) used, the means or route of administration of the agent(s), the nature, structure and age of the biofilm, the species of organism to be treated and so on.

The present invention also provides compositions for promoting dispersal of microorganisms from a biofilm, for inducing programmed cell death in a microorganism, for inhibiting biofilm formation and/or development and for increasing the susceptibility of microorganisms to antimicrobial agents. Typically the compositions provide means for carrying out the methods of the invention.

The methods and compositions of the invention described above find application in a wide range of environments and circumstances. The following is a brief discussion of some general areas of application of these methods and compositions. However those skilled in the art will readily appreciate that any environment or situation in which biofilm development is a problem or in which it is desirable to inhibit microbial growth will be potentially suitable for these methods and compositions.

One area of application of methods and compositions of the invention is in marine, brackish water and freshwater anti-fouling paints or coatings, for example in treating ship hulls, aquaculture equipment, fishing nets or other in-water structures. The methods and compositions also find application in a range of industrial and domestic applications, including but not limited to water supply reservoirs and feed pipes, drain pipes (domestic or industrial scale), process equipment of, for example, cooling towers, water treatment plants, dairy processing plants, food processing plants, chemical manufacturing plants, pharmaceutical or biopharmaceutical manufacturing plants, oil pipelines and oil refinery equipment, and pulp and paper mills.

Compositions of the invention may also be used in coating medical devices, including implantable medical devices, including but not limited to venous catheters, urinary catheters, stents, prostheses such as artificial joints, hearts, heart valves or other organs, pacemakers, surgical plates and pins and contact lenses. Other medical equipment may also be coated, such as catheters and dialysis equipment. Methods and compositions of the invention also find application in the management of infectious diseases. For example, a variety of bacterial infections associated with biofilm formation may be treated with methods and compositions of the invention, such as cystic fibrosis, otitis media, bacterial endocarditis, kidney stones, legionnaire's disease, urinary tract infections, pulmonary infections, dental plaque, dental caries and infections associated with surgical procedures or burns. Accordingly, compositions of the invention may be formulated as pharmaceutical compositions or form components of, for example, surgical dressings, mouthwash, toothpaste or saline solutions.

Compositions according to the invention may be applied or coated onto, or incorporated in the surface of an object/item of interest well in advance of use of said object/item in, or exposure of said object/item to an environment which comprises biofilm-forming microorganisms, or a composition of the invention may be applied or coated onto, or incorporated in the surface of an object/item of interest immediately before use of that object/item in, or exposure of said object/item to an environment which comprises biofilm-forming microorganisms.

Compositions according to the invention may be in any suitable form. For example a composition of the invention may be formulated as a paint, wax, other coating, emulsion, solution, gel, suspension, beads, powder, granules, pellets, flakes or spray. The skilled addressee will recognise that the appropriate formulation will depend on the particular application and the proposed route of delivery.

Compositions of the invention typically also include carriers, diluents or excipients. Suitable carriers, diluents and excipients are known to those skilled in the art. The diluents, adjuvants and excipients must be "acceptable" in terms of being compatible with the other ingredients of the composition, and in the case of pharmaceutical compositions, not deleterious to the recipient thereof.

Carriers may be liquid or solid. In the case of liquid carriers, the liquid may be an aqueous or non-aqueous solvent. Typically for anti-fouling and other industrial applications, the composition, for example in the form of a paint or other surface coating, employs a carrier enabling the controlled release of the active agent temporally and/or spatially. A variety of methods to achieve controlled release of bioactive agents are known to those skilled in the art and may include, for example, encapsulation of the active agent in a suitable polymer or polymer-based product. The polymer may be an organic or inorganic polymer, for example a polyolefin, polyether, polyester, polyamide, polyurethane or polypeptide. Suitable polymers for providing controlled release are known to those skilled in the art, for example as disclosed in U.S. Pat. No. 6,610,282, the disclosure of which is incorporated herein by reference.

Typically, the rate of release of the substance is determined by the properties of the polymer itself as well as environmental factors (such as pH, temperature etc). Controlled release systems are capable of delivering substances slowly and continuously for up to several years. Those skilled in the art will appreciate that a number of controlled release systems are applicable to the delivery of agents according to the present invention. By way of example only, release may be diffusion controlled, chemically controlled or solvent activated.

In diffusion controlled systems, diffusion of the agent trapped within a polymer matrix is the rate-determining factor for the overall release rate. One type of diffusion controlled system employs a reservoir device in which the agent forms a core surrounded by an inert diffusion barrier. These systems include membranes, capsules, microcapsules, liposomes, and hollow fibers. Alternatively the device may be a monolithic device in which the active agent is dispersed or dissolved in an inert polymer. Diffusion through the polymer matrix is the rate-limiting step, and release rates are determined in part by the choice of polymer and its consequent effect on the diffusion and partition coefficient of the agent to be released.

In typical chemically controlled systems a polymer degrades over time and releases an agent in an amount proportional to the gradual erosion. Chemical control can be achieved using bioerodible or pendant chains. In a bioerodible system the agent is ideally distributed uniformly throughout a polymer in the same way as in monolithic diffusion systems. As the polymer surrounding the agent is eroded, the agent escapes. In a pendant chain system, the agent may be covalently bound to the polymer by a chemistry allowing for release by any desired and practicable physical or chemical means known in the art such as by, for example, bond scission owing to water or enzymes.

In typical solvent-activated controlled systems, the active agent (which may be nitric oxide, a nitric oxide generating or releasing agent, or a nitric oxide scavenger or an antioxidant) is dissolved or dispersed within a polymeric matrix and is not able to diffuse through that matrix. Osmotic pressure is used as the driving force for release of the agent. In one type of solvent-controlled system, as the environmental fluid (e.g., water) penetrates the matrix, the polymer (e.g. a hydrogel) swells and its glass transition temperature is lowered below the environmental (host) temperature. Thus, the swollen polymer is in a rubbery state and allows the active agent contained within to diffuse through the encapsulant.

Chemical bonding of a bioactive agent to a polymer can be accomplished in several general ways based on different methods of synthesis well known to those skilled in the art including: reaction on preformed polymers; reactions on naturally-occurring polymers; polymerization of vinyl monomers containing the active ingredient; and step growth polymerizations. When the bioactive agent is chemically bonded to a polymer, the bond has to be cleaved by a chemical reaction-typically enzymatic, hydrolytic, thermal, or photochemical. A variety of chemical and physical variables can affect the rate of bond cleavage and subsequent release of chemically attached materials from polymers including the nature of the labile bond, length of the spacer group, molecular weight, hydrophilicity, neighbouring group effects, environmental factors and physical form and dimensions.

In anti-fouling applications, self-polishing antifouling coatings are known in the art. Such coatings are typically based on polymers of tributyltin methacrylate, methyl methacrylate, and film softening monomers such as 2-ethylhexyl acrylate. An organotin polymer typically acts as the paint binder. Such paints may also contain a toxicant additive such as cuprous oxide or a triorganotin compound. In addition, the usual paint additives such as pigments, thixotropic agents may also be present. In normally alkaline seawater, the polymeric organotin binder is gradually hydrolyzed, and the tributyltin is liberated in a form that is an active antifoulant. The hydrolyzed polymer formed is water-soluble or water-swellable and is easily eroded off the surface by moving seawater, exposing a fresh surface of paint.

For pharmaceutical applications, a number of suitable controlled release systems are known in the art. For example, polymeric colloidal particles or microencapsulates (microparticles, microspheres or nanoparticles) in the form of reservoir and matrix devices may be employed, or the agent may be contained by a polymer containing a hydrophilic and/or leachable additive eg, a second polymer, surfactant or plasticiser, etc. to give a porous device, or a device in which the drug release may be osmotically 'controlled' (both reservoir and matrix devices). Large cage-like molecules such as the C60 Buckminster-fullerenes ('Buckyballs') or hyperbranched (starburst) dendrimers may also be used.

Those skilled in the art will readily appreciate that the delivery systems and methods described above are merely examples of suitable methods and systems that may be employed in the present invention. Any other suitable carriers and delivery systems may be employed to achieve the desired means of application of agents according to embodiments of the present invention.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 1% to 99.9% by weight of the compositions.

For pharmaceutical applications, compositions may be formulated for delivery by any route, for example oral, topical, intracavitary, intravesical, intramuscular, intraarterial, intravenous, intranasal, intrapulmonary or subcutaneous.

As the inventors have discovered that nitric oxide and nitric oxide generating or releasing agents result in increased sensitivity of microorganisms to antimicrobial agents, methods of the present invention may be employed in combination with at least one antimicrobial agent. Any suitable antimicrobial agents may be used, for example antibiotics, detergents, surfactants, agents that induce oxidative stress, bacteriocins and antimicrobial enzymes, peptides and phage. The antimicrobial agents may be natural or synthetic. Indeed the antimicrobial agent employed may be selected for the particular application of the invention on a case-by-case basis, and those skilled in the art will appreciate that the scope of the present invention is not limited by the nature or identity of the particular antimicrobial agent. By way of example only, suitable antibiotics include but are not limited to β-lactams, monopenems, carboxypenems, aminoglycosides, quinolones, macrolides, lincozamides, tetracyclines, streptogramins, glycopeptides, rifamicins, sulphonamides chloramphenicol, nalidixic acid, azole-containing compounds and peptide antibiotics. Antimicrobial enzymes include but are not limited to lipases, pronases, lyases (e.g. alginate lyases) and various other proteolytic enzymes and nucleases.

It will be readily appreciated by those skilled in the art that according to the methods of the invention each component of the combination may be administered at the same time, or sequentially in any order, or at different times, so as to provide the desired effect. Alternatively, the components may be formulated together in a single dosage unit as a combination product. Accordingly, compositions of the invention may comprise, in addition to nitric oxide and/or at least one nitric oxide generating or releasing agent, at least one antimicrobial agent.

As described herein, the present inventors have also found that use of a nitric oxide scavenger reverses the effect observed with the nitric oxide donor SNP on biofilm and planktonic growth, thereby providing avenues for the inhibition of programmed cell death and inhibition of cell dispersal from biofilms and the maintenance and/or enhancement of activity of biofilms in circumstances where this is beneficial.

Accordingly, aspects of the present invention relate to methods for maintaining and/or enhancing the functioning of a biofilm, wherein the biofilm is exposed to at least one nitric oxide scavenger and/or at least one antioxidant. The invention also relates to methods for inhibiting programmed cell death in a microorganism, wherein the biofilm is exposed to at least one nitric oxide scavenger and/or at least one antioxidant. The present invention further provides compositions for carrying out the above methods.

Thus, methods and compositions of the invention enable the manipulation of biofilm longevity, viability, density, activity and/or efficacy via the use of nitric oxide scavenging molecules and RONS-quenching molecules. Agents suitable for maintaining and/or enhancing the functioning of a biofilm or inhibiting programmed cell death include nitric oxide scavengers such as 2-phenyl-4,4,5,5-tetramethyl-imidazoline-1-oxyl 3-oxide (PTIO), carboxy-PTIO, N-(dithiocarboxy)sarcosine (DTCS), N-methyl-D-glucamine dithiocarbamate (MGD), (+)-rutin hydrate and haemoglobin, and antioxidants such as thioredoxin, superoxide dismutase, glutathione and ascorbic acid. Those skilled in the art will readily appreciate that a number of other nitric oxide scavengers and antioxidants known in the art are equally applicable to the present invention, and the present invention is not limited by the identity of the particular agents used. Indeed the selection of the appropriate agent for a particular application of the invention may be made on a case-by-case basis. Compositions containing such agents may be formulated as described above.

Those skilled in the art will appreciate that the methods and compositions of the present invention relating to biofilm regulation are applicable to single species or mixed species biofilms. Bacterial species to which the present invention relates may be any species capable of forming a biofilm or contributing to a biofilm. Targeted microbial species may include fungi, including yeasts and filamentous fungi, and Gram positive and Gram negative bacteria. Biofilms of interest to the present invention may comprise microorganisms selected from, but not limited to *Candida* spp. (including *C. albicans*), *Hormoconis* spp. (including *H. resinae*), *Pseudomonas* spp. such as *P. aeruginosa*, *Pseudoalteromonas* spp. such as *P. tunicata*, *Staphylococcus* spp. such as *S. aureus* (including methicillin-resistant and vancomycin-resistant *S. aureus*) and *S. epidermidis*, *Streptococcus* spp. such as *S. mutansl S. sobrinus*, *Shigella* spp. such as *S. flexeri*, *S. dysenteria*, *Mycobacterium* spp. such as *M. tuberculosis*, *Enterococcus* spp. such as *E. faecalis*, *Escherichia* spp. such as *E. coli*, *Salmonella* spp. such as *S. typhimurium*, *S. typhi* and *S. enteritidis*, *Legionella* spp. such as *L. pneumophila*, *Haemophilus* spp. such as *H. influenzae*, *Bacillus* spp. such as *B. licheniformis*, sulfate-reducing and iron-reducing bacteria (such as *Desulfovibrio* spp., including *D. vulgaris* and *D. desulfuricans*, *Shewanella* spp., including *S. putrefaciens*, *Geobacter* spp., including *G. metallireducens*), *Klebsiella* spp. such as *K. pneumoniae*, *Proteus* spp. such as *P. mirabilis*, *Aeromonas* spp., *Arthrobacter* spp., *Micrococcus* spp., *Serratia* spp. such as *S. marcescens*, *Porphyromonas* spp. such as *P. gingivalis*, *Fusobacterium* spp., such as *F. nucleatum* and *Vibrio* spp. such as *V. cholerae*. The microbial species may be aerobic, anaerobic, facultative, aerotolerant, aerophobic, or microaerophilic. Alternatively those skilled in the art will appreciate that in some applications of the present invention, the identities of the particular species in the mixed communities of the biofilm to be treated are undetermined and are not critical to the applicability of the invention.

The present invention will now be further described in greater detail by reference to the following specific examples, which should not be construed as in anyway limiting the scope of the invention.

EXAMPLES

For the biofilm studies described in Example 1 to 3, *Pseudomonas aeruginosa* strains PAO1 and PAO1-GFP, containing a chromosomal insertion of green fluorescent protein (GFP), generously donated by Marie Allesen-Holm, were used. Overnight cultures were routinely performed in Luria Bertani (LB) medium, with shaking at 37° C. Biofilm and planktonic experiments were conducted in modified M9 minimal medium as described elsewhere (Webb et al., 2003, Cell death in *Pseudomonas aeruginosa* biofilm development, *J. Bacteriol.*, 185: 4585-4592) with 5 mM glucose for continuous culture experiments and 20 mM for batch experiments.

Example 1

Cell Death and Dispersal in Biofilms Correlate with the Accumulation of Peroxynitrite in Mature Microcolonies

*P. aeruginosa* PAO1 were grown in continuous culture flow cells (channel dimensions, 1×4×40 mm) at room temperature as previously described (Moller et al., 1998, In situ gene expression in mixed-culture biofilms: evidence of metabolic interactions between community members, *Appl. Environ. Microbiol.*, 64: 721-732) for biofilm generation. Channels were inoculated with 0.5 mL of overnight cell cultures and incubated without flow for 1 hour at room temperature. Flow was then started with a mean flow velocity in the flow cells of 0.2 mm·s$^{-1}$, corresponding to laminar flow with a Reynolds number of 0.02.

To investigate cell death during biofilm development, biofilms were stained with the LIVE/DEAD BacLight bacterial viability kit (Molecular Probes) in which SYTO9 is used to specifically stain live cells and propidium iodide is used to specifically stain dead cells. Stock solutions of the stains were diluted to 3 µL·mL$^{-1}$ in modified M9 medium and injected into the flow channels. Live SYTO 9-stained cells and dead propidium iodide-stained cells were visualized with a confocal laser scanning microscope (Olympus) with fluorescein isothiocyanate and tetramethyl rhodamine isocyanate optical filters, respectively. It was observed that after 7 days, biofilms of *P. aeruginosa* undergo highly reproducible patterns of cell death and dispersal, and that these events lead to the formation of hollow colonies within biofilms (FIG. 1A—white arrow points to hollow structure; black arrow points to dead cells).

To investigate the role of specific reactive and nitrogen species (RONS) and detect specific RONS that accumulate in biofilms structures during death and dispersal, a series of reactive fluorescent dyes, each targeting a different RONS, were injected in the flow channels and were incubated 30 minutes in the dark before confocal laser scanning microscopy. The RONS investigated were nitric oxide (NO), peroxynitrite (ONOO—), hydrogen peroxide ($H_2O_2$) and superoxide radicals ($O_2$—.). DAFFM-DA (Molecular Probes), 5 mM stock in DMSO, was used at 100 µM for the detection of nitric oxide (Kojima et al., 1999, Fluorescent indicators for imaging nitric oxide production, *Angew. Chem. Int. Ed. Engl* 38: 3209-3212), Dihydrorhodamine 123 (DHR) (Sigma), stock 2.5 mg·mL$^{-1}$ in ethanol, was used at 15 µM for the detection of peroxynitrite (Crow, 1997, Dichlorodihydrofluorescein and dihydrorhodamine 123 are sensitive indicators of peroxynitrite in vitro: implications for intracellular measurement of reactive nitrogen and oxygen species, *Nitric Oxide*, 1: 145-157), carboxy-$H_2$DCF-DA (Molecular Probes), 10 mM stock in DMSO, was used at 100 µM for the detection of hydrogen peroxide, and hydroethidine (HEt) (Sigma), 1 mg·mL$^{-1}$ stock in 1% DMSO in Phosphate Buffered Saline (PBS), was used at 10 µM for the detection of superoxide radicals (Bindokas et al., 1996, Superoxide production in rat hippocampal neurons: selective imaging with hydroethidine, *J. Neurosci.* 16: 1324-1336). Stock solutions were kept frozen and covered from light. Final solutions were freshly made in modified M9 medium before use.

As shown in FIG. 1B, the bacteria in the biofilm showed a low level of autofluorescence, revealed by the control images. Positive fluorescence was detected with two of the RONS-specific dyes: HEt detecting superoxide radicals, $O_2$—. and, at considerably higher level of fluorescence, DHR detecting peroxynitrite, ONOO—. The light field images (left panel) revealed that the fluorescence occurred in mature microcolonies that had undergone death and dispersal events as shown in FIG. 1A. The negative results obtained with $H_2$DCF, for the detection of hydrogen peroxide, correlate with the overexpression of catalase previously reported in *P. aeruginosa* biofilms (Stewart et al., 2000, Effect of catalase on hydrogen peroxide penetration into *Pseudomonas aeruginosa* biofilms, *Appl. Environ. Microbiol.* 66: 836-838). DHR is specific to peroxynitrite and cannot be oxidized by other RONS alone (Crow et al., 1999). Because peroxynitrite is the direct product of superoxide and nitric oxide, it was surprising not to detect nitric oxide with DAFFM. However, nitric oxide is extremely reactive, and the reaction between nitric oxide and superoxide is known to occur instantaneously, in a diffusion-limited manner (Kelm et al., 1997, The nitric oxide/superoxide assay. Insights into the biological chemistry of the NO/$O_2$-interaction, *J. Biol. Chem.* 272: 9922-9932), which may prohibit the detection of nitric oxide with DAFFM.

The results presented above demonstrate that the RONS peroxynitrite accumulates in biofilm cells at high cell densities and triggers cell death in microcolonies within mature biofilms.

Example 2

Biofilm Versus Planktonic Growth in *P. Aeruginosa* is Regulated by Nitric Oxide Nitric oxide is a widespread intercellular and intracellular signalling molecule in biological systems. It is also the key precursor of peroxynitrite, a potent oxidant with a wide range of biological effects. Nitric oxide readily reacts with superoxide to yield peroxynitrite:

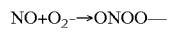

The inventors therefore investigated the effect of the nitric oxide donor, sodium nitroprusside (SNP), on planktonic and biofilm growth of *P. aeruginosa*. SNP releases nitric oxide in vivo (Smith et al., 2001, Mechanisms of nitric oxide release from nitrovasodilators in aqueous solution: reaction of the nitroprusside ion ([Fe(CN)$_5$NO]$_2$—) with L-ascorbic acid, *J Inorg Biochem*, 87: 165-173).

Biofilms in 96-well plates were used for these experiments. 100 µL of 1/1000 overnight cultures of PAO1-GFP diluted in modified M9 medium were inoculated in 96-well plates (Sarstedt) and grown for 24 hours, at 37° C. with 120 rpm shaking. SNP was added to the cultures at concentrations of between 25 nM and 100 mM. 4 replicates per treatment were used. After overnight growth, the supernatant was transferred to wells of a new plate. The wells were washed twice with PBS and stained for 20 minutes with 120 µL of crystal violet. The wells were then washed again three times with PBS and diluted in 120 µL of absolute ethanol. Biofilm formation was quantified by measurement of OD$_{490\ nm}$, and planktonic growth was quantified by fluorescence measurement.

Figure 2:
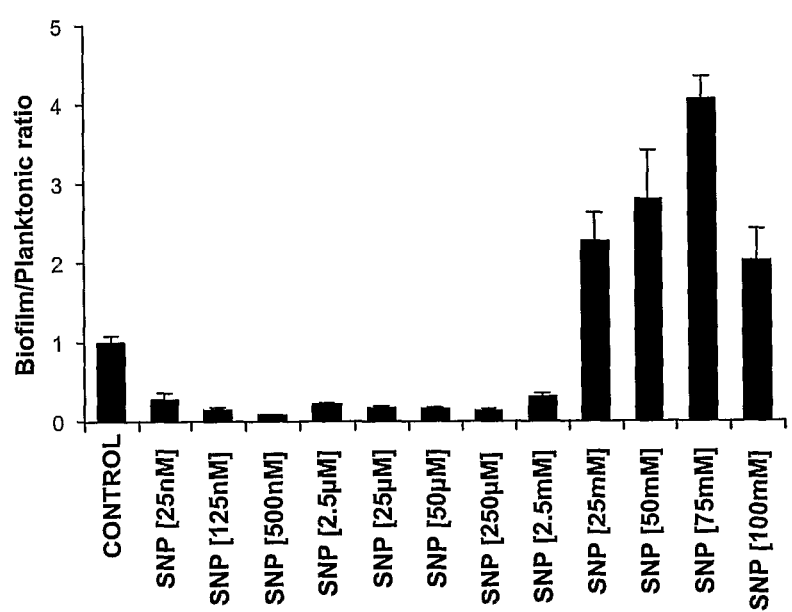
FIG. 2. The effect of administration of SNP on biofilm and planktonic growth of *P. aeruginosa*. PAO1 cells were grown for 24 hours in 96-well plates in the presence of sodium nitroprusside (SNP). Planktonic growth was quantified by fluorescence measurement and biofilm formation by crystal violet staining. Control, no SNP added.

As shown in FIG. 2, at high concentrations (in the millimolar range) an increase in biofilm formation and a decrease in planktonic growth was observed (25 mM-100 mM SNP) in comparison to untreated biofilm. At these concentrations, SNP is toxic to various bacterial species; the SNP releases high, toxic concentrations of nitric oxide (Joannou et al., 1998, Characterization of the bactericidal effects of sodium nitroprusside and other pentacyanonitrosyl complexes on the food spoilage bacterium *Clostridium sporogenes, Appl Environ Microbiol*, 64: 3195-3201; Kelley et al., 1998, Inducible nitric oxide synthase expression is reduced in cystic fibrosis murine and human airway epithelial cells, *J Clin Invest*, 102: 1200-1207). At lower concentrations, in the micromolar and nanomolar ranges, a decrease in biofilm formation and an increase in planktonic growth was observed. The highest effect was repeatedly observed with 500 nM SNP and this concentration was used for subsequent experiments described in this Example and Example 3.

Figure 3:
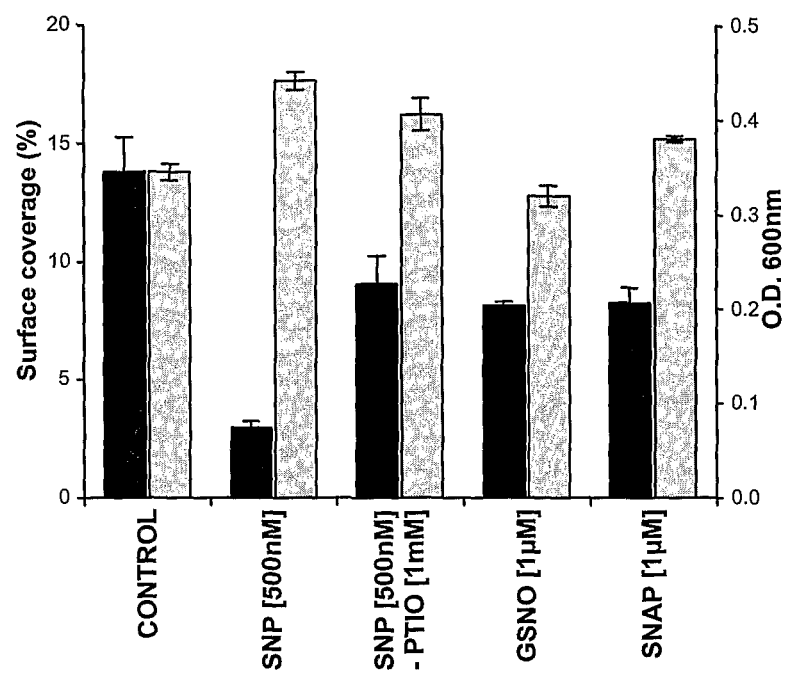
FIG. 3. The effect of nitric oxide generating or releasing agents on the transition from biofilm to planktonic growth in *P. aeruginosa*. PAO1 cells were grown for 24 hours in petri dishes containing microscope slides in the presence of a nitric oxide donor, sodium nitroprusside (SNP), S-nitroso-L-glutathione (GSNO) or S-nitroso-N-acetylpenicillamine (SNAP) or SNP plus the nitric oxide scavenger 2-phenyl-4, 4,5,5-tetramethyl-imidazoline-1-oxyl 3-oxide (PTIO). Planktonic growth was quantified by measuring the optical density ($OD_{600\,nm}$) of the supernatant (light bars) and biofilm growth by measuring the percentage of surface coverage (dark bars) using image analysis of digital photomicrographs of microscope slides after staining.

To confirm the role of nitric oxide in the observed events, two different nitric oxide donors, S-nitroso-L-glutathione (GSNO) and S-nitroso-N-acetylpenicillamine (SNAP) were used in place of SNP, each at concentrations of 1 µM. As illustrated in FIG. 3, similar to SNP, both of these nitric oxide donors also produced decreases in biofilm formation and increases in planktonic growth, although to a lesser extent than was observed with SNP.

These results suggest that at low concentrations, nitric oxide signals a transition from biofilm to planktonic phenotype.

FIG. 3 also shows the effect of the nitric oxide scavenger 2-phenyl-4,4,5,5-tetramethyl-imidazoline-1-oxyl 3-oxide (PTIO). PTIO was added to a growing biofilm at 1 mM concentration in addition to SNP at 500 nM. The addition of PTIO reduced the SNP effect by 40% or more in both planktonic and biofilm phenotypes.

Example 3

Exposure to Low Levels of Nitric Oxide Increases the Sensitivity of *P. aeruginosa* Cells to Antimicrobial Agents Planktonic cells are known to be up to 1000 times more sensitive towards antibiotics than biofilm cells (Brooun et al., 2000, A dose-response study of antibiotic resistance in *Pseudomonas aeruginosa* biofilms, *Antimicrob Agents Chemother*, 44: 640-646; Davies, 2003, Understanding biofilm resistance to antibacterial agents, *Nat Rev Drug Discov*, 2: 114-122). One of the major difficulties in combating mature biofilms is this reduced sensitivity to antimicrobial agents. The results described above in Example 2 demonstrate that nitric oxide promotes the planktonic mode of growth over the more resistant biofilm phenotype. The inventors therefore investigated whether nitric oxide exposure may also restore antimicrobial sensitivity to biofilm cells. The effects of various antimicrobial agents on *P. aeruginosa* biofilms and planktonic cells that were exposed to low levels of nitric oxide were examined.

To test the sensitivity of cells, a broad range of antimicrobial compounds were examined: the antibiotic tobramycin (Sigma) that irreversibly inhibits bacterial protein synthesis, used at a final concentration of 100 µM; the surfactant sodium dodecyl sulphate (SDS) used at 0.1%; and the oxidative stress inducing agents hydrogen peroxide ($H_2O_2$; at 10 mM concentration) and hypochlorous acid (HOCl; at 8 mM concentration).

Biofilms were grown in petri dishes containing microscope glass slides (76×26 mm, Superfrost, Menzel Gläser). To prevent contamination, the slides were autoclaved and the petri dishes sterilised by 30 minutes exposure to ultraviolet. 25 mL of 1/1000 overnight cultures of PAO1-GFP diluted in modified M9 medium were inoculated in the plates and grown for 24 hours, at 37° C. with 50 rpm shaking, allowing biofilm formation on the slides. $OD_{600\,nm}$ readings of the supernatant were determined. The slides were then rinsed in sterile PBS. For the antimicrobial sensitivity assays, the slides were incubated with modified M9 medium alone (negative control), or with 500 µL of the antimicrobial agent diluted in modified M9 medium, for 30 minutes in a humid chamber and rinsed again in PBS. The biofilms on the slides were stained with 250 µL of LIVE/DEAD staining as described above for 20 minutes in a humid chamber. Seven confocal pictures per slide were randomly taken and the percentage of surface coverage was quantified with image analysis.

Figure 4:
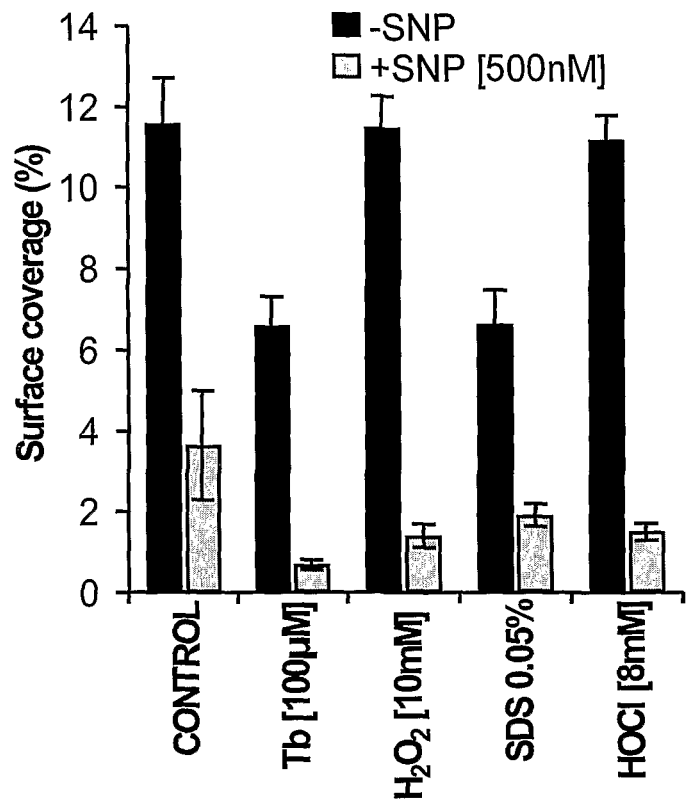
FIG. 4. The effect of SNP treatment on the sensitivity of *P. aeruginosa* to anti-microbial agents. *P. aeruginosa* PAO1 was grown for 24 hours in petri dishes containing microscope slides in the presence or absence of 500 nM SNP. Biofilms on microscope slides were treated for 30 minutes with the anti-microbial solutions, stained with LIVE/DEAD staining to allow analysis with light microscopy and quantified (percentage surface coverage) using digital image analysis. (A) Sensitivity of biofilms (% surface coverage) on microscope slides to antimicrobials tobramycin (Tb), hydrogen peroxide ($H_2O_2$), sodium dodecyl sulphate (SDS) and hypochlorous acid (HOCl) in the presence (light grey bars) or absence (dark grey bars) of SNP. (B) Confocal fluorescence micrographs of the same slides after treatment.
Figure 4:
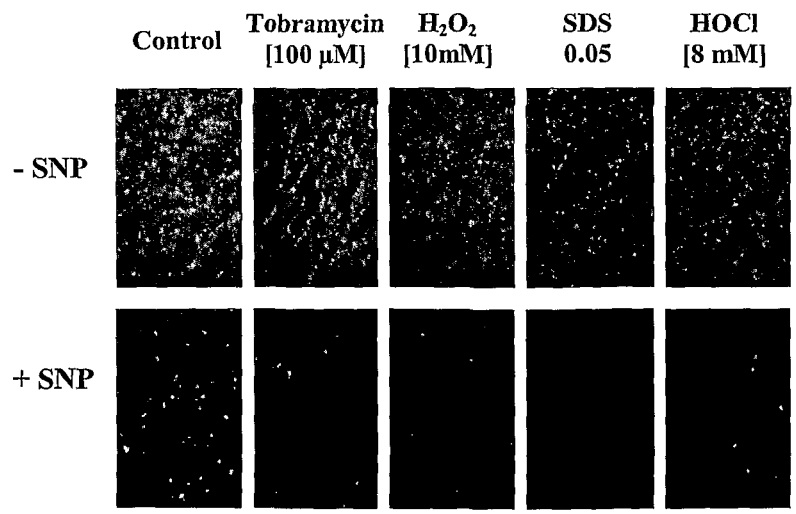

A dramatic reduction, up to 95%, in the number of biofilm cells after the combination treatments (SNP and an antimicrobal agent) was reproducibly observed (FIGS. 4A and 4B). The highest effect was obtained with tobramycin, an antibiotic commonly used to treat cystic fibrosis patients.

Figure 5:
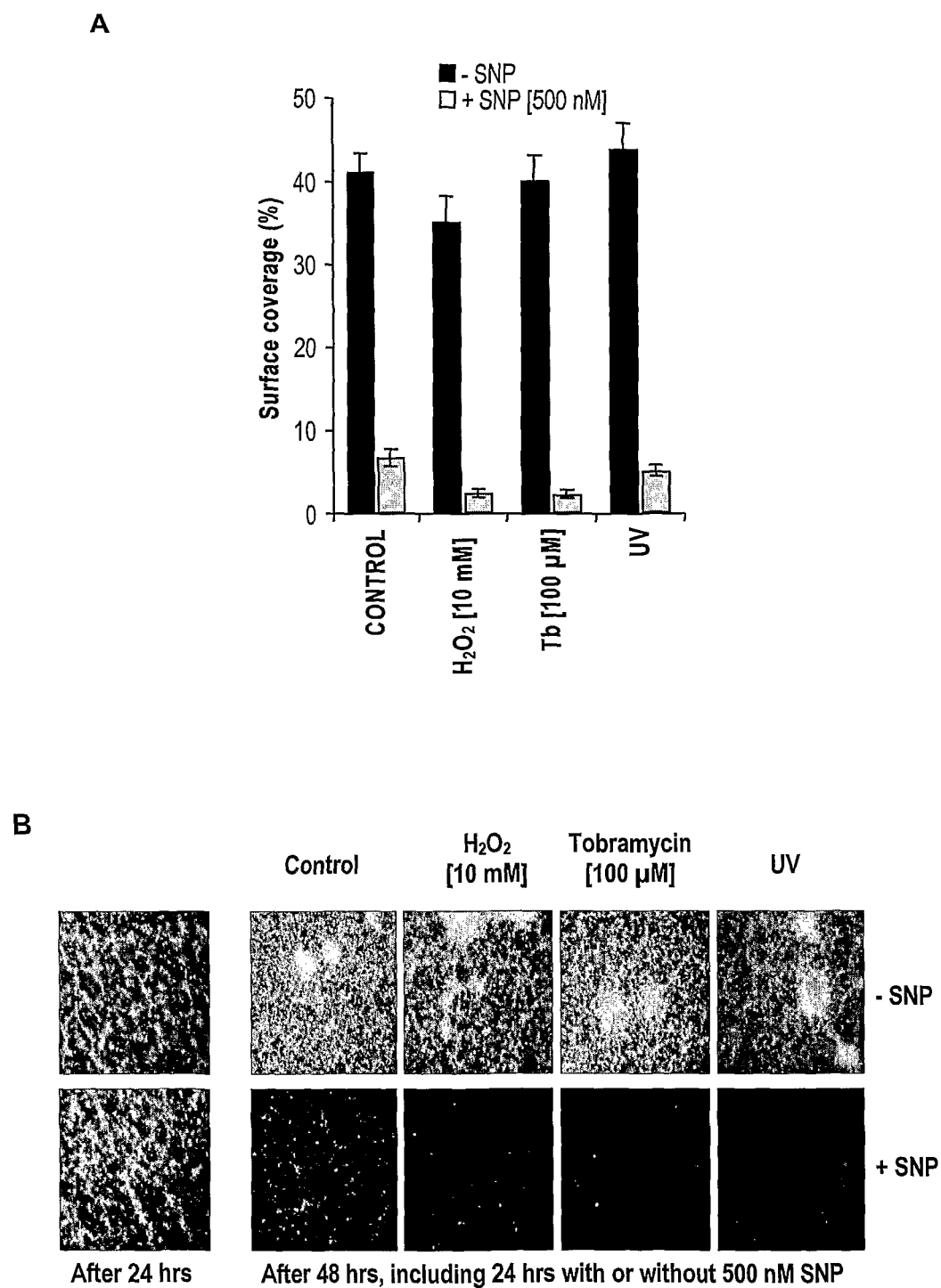
FIG. 5. The effect of SNP treatment on the sensitivity of pre-established *P. aeruginosa* biofilms to anti-microbial agents. *P. aeruginosa* PAO1 was grown for 24 hours in petri dishes containing microscope slides for 24 hours prior to the addition of 500 nM SNP. Biofilms were grown for a further 24 hours and then treated for 30 minutes with the antimicrobial solutions, stained with LIVE/DEAD staining to allow analysis with light microscopy and quantified (percentage surface coverage) using digital image analysis. (A) Sensitivity of biofilms (% surface coverage) on microscope slides to tobramycin (Tb), hydrogen peroxide ($H_2O_2$) and ultraviolet light (UV) in the presence (light grey bars) or absence (dark grey bars) of SNP. (B) Confocal fluorescence micrographs of the same slides after treatment.

The ability of SNP to increase the sensitivity of pre-established *P. aeruginosa* biofilms was also investigated, as illustrated in FIG. 5. Biofilms were grown as described above, with the exception that the initial 24 hours of development was in the absence of SNP. After 24 hours, the media was changed and replaced with media containing 500 mM SNP (in treatment biofilms; SNP absent in controls). Biofilms were grown for a further 24 hours prior to the addition of either Tb at 100 µM or $H_2O_2$ at 10 mM for 30 minutes or exposure to UV light (19 W, 254 nm for 30 min, 30 cm from the lamp). Sensitivity was determined as described above with respect to FIG. 4. As shown in FIG. 5, a dramatic reduction in biofilm surface coverage and the number of biofilm cells was observed following combination treatment of pre-established biofilms.

Figure 6:
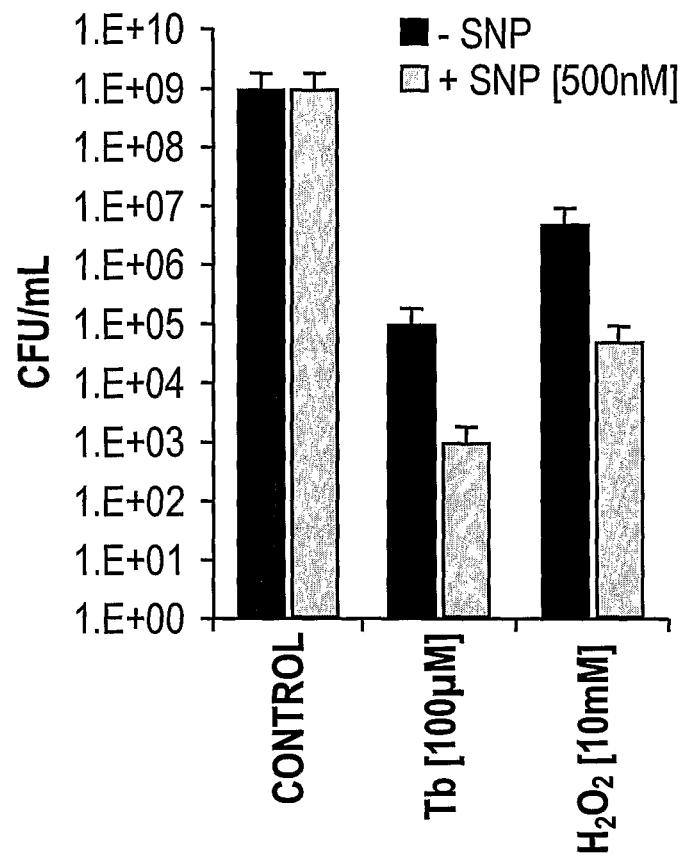
FIG. 6. Combination treatment of planktonic *P. aeruginosa* cells using SNP and anti-microbial agents. Planktonic cells were treated for 2 hours with the antimicrobial agent tobramycin (Tb) or hydrogen peroxide ($H_2O_2$). Plate counts of colony forming units (log CFU/mL) were performed to assess the viability of the bacteria.

To investigate the effect of combination treatment of SNP and an antimicrobial agent on planktonic cells, overnight cultures of PAO1-GFP were diluted 1/1000 in modified M9 medium containing 20 mM of glucose with or without 500 nM SNP. After 24 hours the cells were diluted 1/10 in the antimicrobial solution and incubated 2 hours at room temperature. CFU plate counts were performed to assess the viability of the bacteria. The SNP pre-treatment on planktonic cells resulted in a further 2 log decrease in CFU counts after $H_2O_2$ and tobramycin exposures when compared to untreated *P. aeruginosa* cells (FIG. 6). Interestingly, although treatment with 500 nM SNP caused an increase in the optical density of planktonic cultures compared to untreated controls (FIG. 3), an equivalent increase in CFU counts (viability) was not observed following exposure to tobramycin or hydrogen peroxide with SNP pre-treatment.

Without wishing to be bound by theory, the inventors suggest the results described above indicate that nitric oxide induces a planktonic "dispersal" physiology in *P. aeruginosa* biofilms and therefore enhances their sensitivity to antimicrobial agents.

Example 4

Nitric Oxide Induces Dispersal of Cells in Floc Biofilms

In view of the results described in Example 2 for surface-associated biofilms, the ability of nitric oxide to induce dispersal from a non surface-associated mixed species biofilm was investigated.

Four parallel bioreactors (30 mL flasks) were operated under acetate-fed denitrifying conditions (anoxic) for 13 days in batch feeding mode (1 decant and feed cycle/day). The aim of these experiments was to demonstrate that externally-supplemented NO, generated by SNP can influence sludge flocculation, cell death and dispersal in an activated sludge floc (biofilm) system.

The bioreactors were seeded with activated sludge collected from St Marys Sewage Treatment Plant (STP) (Sydney, NSW, Australia) on 18 Nov. 2004. The bioreactors were operated under anoxic conditions at room temperature. Anoxic conditions were maintained by the flushing/sparging of $N_2$ gas into the sludge after feeding with a mixture of 3 mL acetate medium and 12 mL nitrite medium, in addition to 1 mL of SNP/water to achieve the desired concentrations. The bioreactors were operated on a 24 hour cycle, which consisted of 23.5 hour of anoxic reaction followed by a 10 minute settling and decant of 15 mL of supernatant.

The medium for the bioreactors was made up of two components: a carbon medium base; and a nitrogen medium base. For each cycle, the medium consisted of 1 volume of the carbon medium base and 4 volumes of the nitrogen medium base. The carbon medium base comprised (per liter) 6.587 g $CH_3COONa$, 0.042 g $CaCl_2.2H_2O$, 0.090 g $MgSO_4.7H_2O$, 0.160 g $MgCl_2.6H_2O$, 0.011 g $KH_2PO_4$, 0.026 g $Na_2HPO_4.12H_2O$, 0.122 g Bacto peptone (Difco Laboratories, USA), 0.020 g Bacto yeast extract (Difco Laboratories), 0.025 g $NH_4Cl$, and 0.3 ml nutrient solution as previously described (Bond et al., 1999, Identification of some of the major groups of bacteria in efficient and nonefficient biological phosphorus removal activated sludge systems, *Appl Environ Microbiol*, 65: 4077-84). The medium was made up with Milli-Q water and sterilised by autoclaving.

The nitrogen medium base comprised (per liter) 8.972 g $NO_2Na$ and was made up with reverse-osmosis-deionised water. The acetate:$NO_2$—N ratio in the combined medium was maintained at 2.73:1.

To investigate the role of specific reactive and nitrogen species (RONS) and to detect specific RONS that accumulate in biofilm structures during death and dispersal, a series of reactive fluorescent dyes, each targeting a different RONS (at concentrations outlined in Example 1), were combined with 500 mL of activated sludge taken from St Marys STP and were incubated for 30 minutes in the dark before confocal laser scanning microscopy. The RONS investigated were hydrogen peroxide ($H_2O_2$), nitric oxide (NO), peroxynitrite (ONOO—) as well as superoxide ($O_2$—.) and hydroxyl (OH) radicals. A control sample (with no fluorescent RONS dye present) was used to establish CLSM image collection levels for subsequent fluorescent probes. As shown in Table 1, positive fluorescence was detected with two of the RONS-specific dyes: intracellular hydrogen peroxide, $H_2O_2$— and, at higher levels of fluorescence, DHR123 detecting peroxynitrite, ONOO—.

TABLE 1

Assessment of RONS present in St Marys STP (seed) sludge.

| Fluorescent probe | RONS | Observation |
|---|---|---|
| Control | – | – |
| Amplex Red | Extracellular $H_2O_2$ | + |
| DCF | Intracellular $H_2O_2$ | + + |
| DHR123 | ONOO— | + + + |
| HEt | $O_2$—• | – |
| DAF-FM | NO | + |
| TEMPO-9 | $HO/O_2$— | – |

Figure 7:
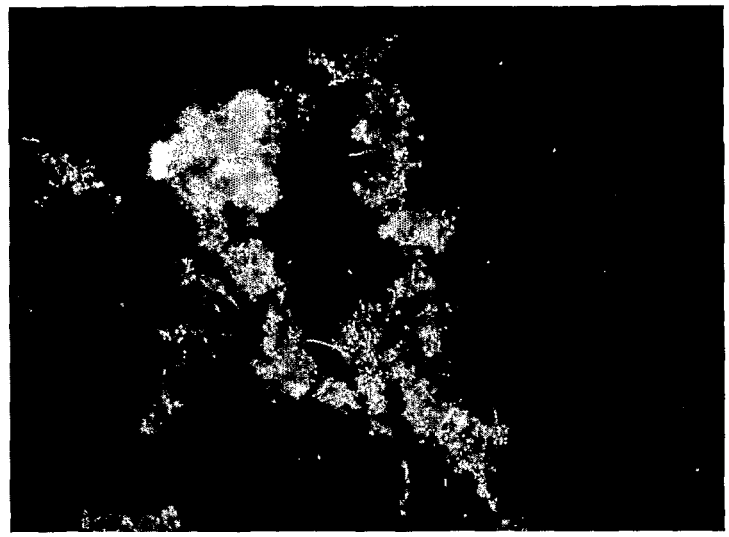
FIG. 7. Effect of SNP exposure on dispersal in floc biofilms from a wastewater treatment sludge reactor. Confocal fluorescence micrographs of 13 day mixed species floc biofilms either untreated (A) or treated with 10 mM SNP (B).
Figure 7:

To investigate and observe sludge flocs and planktonic cells during biofilm development, biofilms were stained with the LIVE/DEAD BacLight bacterial viability kit (Molecular Probes). Stock solutions of the stains were diluted to 1 μL $mL^{-1}$ in 1.5 mL microcentrifuge tubes containing 500 mL of activated sludge samples taken from each bioreactor. Samples (20 μL) were mounted onto glass slides, where cells were visualized with a confocal laser scanning microscope (Olympus). Observations from each bioreactor on day 13 were made for numbers of flocs and planktonic cells. As shown in FIG. 7, substantial dispersal of cells from the treated floc biofilm was observed (FIG. 7B) in comparison to the untreated biofilm (FIG. 7A, Table 2.) after 13 days of SNP treatment.

TABLE 2

Assessment of SNP effect on various sludge parameters after 13 days incubation under anoxic conditions.

| [SNP] | Planktonic cells |
|---|---|
| 0 (control) | + |
| 1 μM | + + |
| 100 μM | + + |
| 10 μM | + + + |

(+ few planktonic cells, <5 cells/field of view; +++ abundant dispersal cells, uncountable, >500 cells/field of view).

The greatest levels of dispersal and floc disruption were observed using an SNP concentration of 10 mM. However, due to the large size of the flocs (in many cases >200 μm) the actual concentration of NO presented to cells inside flocs is likely to be considerably lower. Moreover, the release of NO from the NO donors is dependant on complex chemical reactions and the effective concentration of NO released can be up to 1-2 log lower than the SNP concentrations used (Smith and Dasgupta, 2001, Mechanisms of nitric oxide release from nitrovasodilators in aqueous solution: reaction of the nitroprusside ion ([Fe(CN)5NO]2-) with L-ascorbic acid, *J. Inorg. Biochem.* 87: 165-173).

Example 5

Nitric Oxide Induces Dispersal of Cells in Mixed Species Biofilms 5.1 Materials and Methods
5.1.1 Model Distribution System The biofilm sampling site (BSS) described by Storey and Ashbolt (Storey M. V. and Ashbolt N. J. (2001), "Persistence of two model enteric viruses (B40-8 and MS-2 bacteriophages) in water distribution pipe biofilms", *Water Sci Technol.* 43 (12): 133-8) was used in this study. Model potable and recycled water system biofilms were grown in 2 continuous flow, annular reactors (model 920, BioSurfaces Technologies, Bozeman, Mont.) at the BSS. An annular reactor (AR) consists of a rotating polycarbonate inner cylinder and a stationary glass outer cylinder, separated by a water-filled annular cavity. Sixty stainless steel (SS) and unplasticized polyvinyl chloride (uPVC) coupons (15 mm×40 mm available surface area) were placed on the exposed face of the inner-rotating cylinder of the ARs, which received potable and recycled water respectively, at a rate of 30 L·$h^{-1}$ making the hydraulic retention time 2.2 minutes. The annulus rotation speed was set to provide a linear velocity similar to the mean hydraulic demand of the distribution pipe (0.32 L·$s^{-1}$). Biofilm coupons were sterilized in 1 g·$L^{-1}$ sodium hypochlorite for 2 hours and rinsed with sterile Milli-Q water prior to being placed in each experimental device. Biofilms were allowed to grow on coupon surfaces for a period of 90 days. After this time the inlet flows were stopped and the ARs were enriched with tetracycline and ampicillin resistant *Serratia marcescens* at a final concentration of approximately $10^7$ CFU·mL$^{-1}$. *S. marcescens* cells were allowed to settle in the biofilms on the SS and uPVC coupon surfaces for 2 weeks. Unsettled cells were removed from the system by reconnecting the potable and recycled water inlet flows for one week. *S. marcescens* had previously been harvested from selective LB agar plates (supplemented with 50 µg·mL$^{-1}$ tetracycline and 100 µg·mL$^{-1}$ ampicillin) after 24 hours incubation at 30° C. and washed three times in phosphate buffered saline (PBS).

5.1.2 Experimental Design

Coupons were carefully removed from each biofilm device using sterile forceps. SS coupons (potable) and uPVC coupons (recycled) were removed from each experimental device and transferred to bioreactors in the laboratory for NO exposure. The bioreactors consisted of 1 L polypropylene (PP) beakers with bottom inlet and top outlet covered with aluminium foil and containing PP microscope slide racks (Kartell, Italy) that were modified to fit the coupons. The racks were placed 2 cm above the bottom on a PP stand, and a circular flow was generated with magnetic stirring to simulate the hydraulic shear stress at the wall of a pipe. The bioreactors were sterilized with 1 g·L$^{-1}$ sodium hypochlorite for 2 hours and rinsed with sterile Milli-Q water prior to receiving coupons harboring the biofilms. For each type of biofilm established from potable or recycled water systems, the coupons were randomly placed in 3 separate bioreactors where they were exposed for 18 hours to a continuous flow of autoclaved potable water (sterile and dechlorinated), pH 7.8, containing 0, 100 nM or 500 nM of the NO donor sodium nitroprusside (SNP), at a flow rate of 50 mL h$^{-1}$.

The coupons were then carefully transferred into 25 mL glass vials containing 20 mL of conventional chlorine treatments. A range of chlorine treatments were freshly prepared by diluting 2.4 M hypochlorite solution in ¼ strength Ringers solution and calibrated using a Pocket Colorimeter II (HACH, Loveland, Colo.). After 10 minutes of gentle shaking (75 rpm), the reactions were stopped by adding sodium thiosulfate at a final concentration of 100 µM. For each NO/chlorine combinatorial treatment, triplicate coupons were used for viability counts and duplicate coupons for microscopy analysis.

5.1.3 Analytical Methods

The coupons were processed for viability counts and microscopy analysis.

LIVE/DEAD® BacLight Bacterial Viability Kit (Molecular Probes, Oregon, USA) was used to stain cells in the biofilms. Two stock solutions of stain (SYTO 9 and propidium iodide) were each diluted to a concentration of 3 µL·mL$^{-1}$ in ¼ strength Ringers solution and the coupons were stained with 150 µL of the staining mix and covered with a thin coverslip (10.5×35 mm, ProSciTech, Kirwan, Australia). The coupons were observed under epifluorescence microscopy (Leica model DMR), and biofilm cells were enumerated using an image analysis system (ImageJ, NIH).

For viability counts, the coupons were placed in sterile stomacher bags (101×152 mm) (Seward, UK) containing 25 mL ¼ strength Ringers solution with 100 µM sodium thiosulfate. Bags were heat-sealed and hand rubbed to initiate the disaggregation of attached biofilms. The coupons were sonicated at 400 W (Branson 2210 Sonicator) for 60 s, then stomached for 60 s (Seward Stomacher® 80, Seward, UK) to remove and homogenize remaining biofilm. The homogenate was then aseptically removed from stomacher bags. Heterotrophic plate counts (HPC) were performed using a pour-plate technique on oligotrophic R2A agar (Oxoid, England), and eutrophic Luria Bertani (LB) agar plates. The plates were incubated at 30° C. and counts were carried out after 7 days. *S. marcescens* colonies were morphologically identified and confirmed by plating the colonies on selective LB agar supplemented with 50 µg·mL$^{-1}$ tetracycline and 100 µg·mL$^{-1}$ ampicillin. Sonication and stomaching techniques were previously examined for their efficacy on biofilm removal through the recovery of HPCs.

Analysis of variance (ANOVA) tests at a significance level of 95% were used to compare the impact of the various combinations of low doses of NO, and chlorine disinfectant on biofilm growth.

5.2 Results 5.2.1 Potable Water Biofilms Spiked with *Serratia marcescens*

Figure 8:
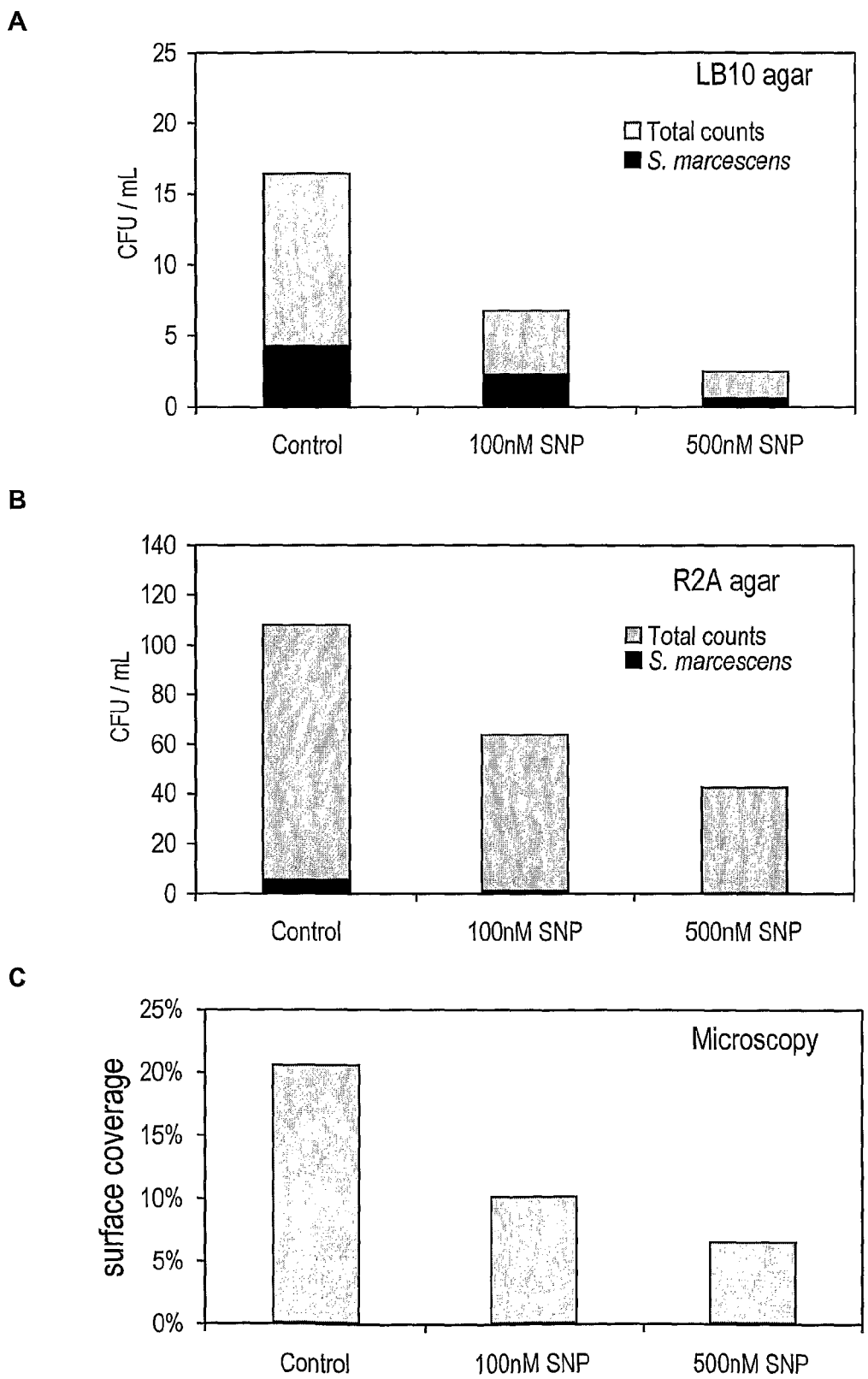
FIG. 8. Drinking water biofilms spiked with *S. marcescens*—effect of SNP on the biofilms after 18 hours exposure to 0, 100 nM or 500 nM SNP: (A) viability counts on oligotrophic agar (R2A, triplicates); (B) viability counts on eutrophic agar ($LB_{10}$, triplicates); (C) percentage of surface coverage using microscopy analysis (BacLight, duplicates).

The data, as illustrated in FIGS. 8A to 8C demonstrates that SNP treatment was effective at removing mixed species biofilms established in a model potable water distribution system as well as *S. marcescens* in a dose dependent manner. Consistent results were obtained from viability assays and microscopy analysis (FIG. 8). The relative proportions of different colony morphologies on the plates were not affected by the SNP treatments, suggesting that this treatment was not selective for specific species within the mixed community. The most efficient treatment concentration was 500 nM SNP, which correlates with previous results observed with *Pseudomonas aeruginosa* and other monospecies bacterial biofilms. In this experiment, free chlorine treatment was used at 2 ppm and complete removal of biofilms was observed on all coupons that were exposed to conventional chlorine.

5.2.2 Recycled Water Biofilms Spiked with *Serratia marcescens*

Figure 9:
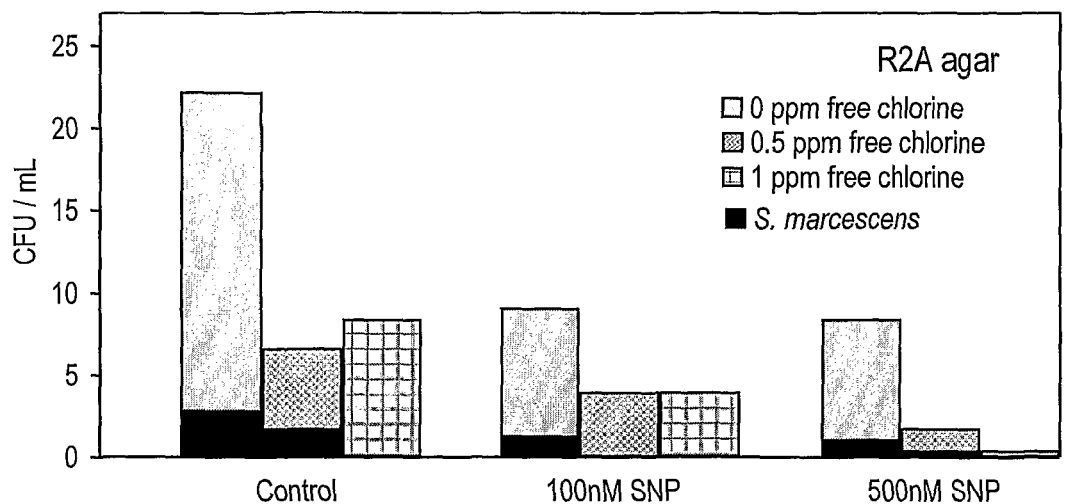
FIG. 9. Biofilms grown for 3 months on uPVC coupons in AR in-line with recycled water distribution system and spiked with *S. marcescens*. Effect of exposure of the biofilms to 0, 100 nM and 500 nM SNP for 18 hours before a 10 minutes treatment with a range of concentration of free chlorine: (A) viability counts on eutrophic agar ($LB_{10}$, triplicates); (B) percentage of surface coverage using microscopy analysis (BacLight, duplicates).
Figure 9:
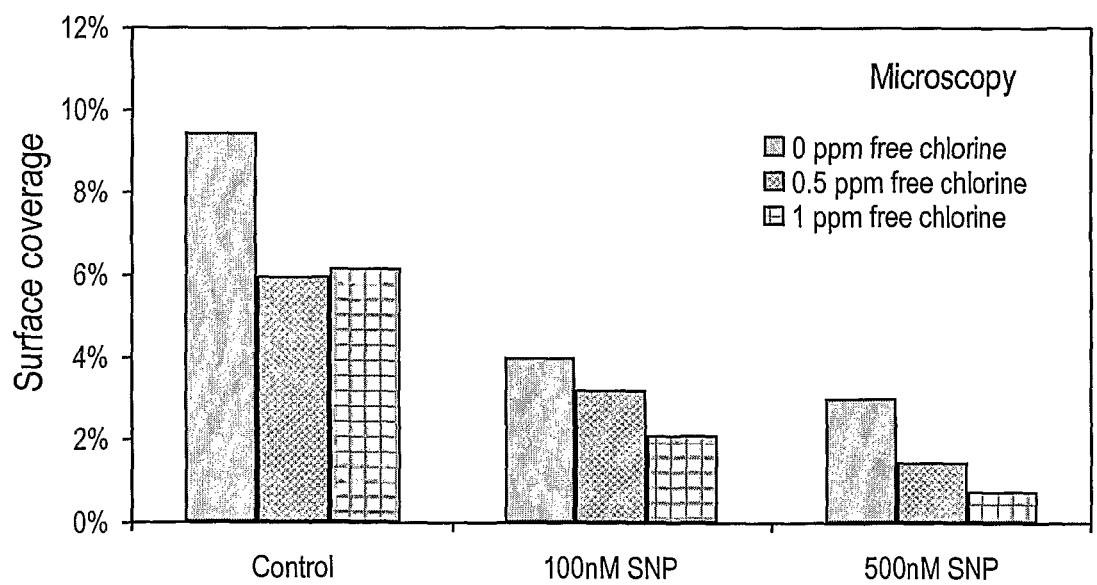

Mixed species biofilms established from a model recycled water distribution system and harboring *S. marcescens* were also reduced in both total counts and *S. marcescens* counts upon exposure to nanomolar concentrations of the NO donor SNP in a dose dependent manner. Consistent results were obtained from viability assays and microscopy analysis (FIG. 9). Biofilms exposed to 500 nM SNP also exhibited increased sensitivity to free chlorine treatments and, for example, 1 ppm free chlorine was up to 20-fold more efficient at removing SNP treated biofilm compared to control biofilms as determined by viability counts (FIG. 9).

Example 6

Low Levels of Nitric Oxide to Induce Dispersal of *S. marcescens, V. cholerae, E. coli* and *B. licheniformis* biofilms Bacterial biofilms were grown in petri dishes (90 mm diameter) containing either glass (Superfrost, Menzel Glaser) or polycarbonate microscope glass slides (76×26 mm,). To prevent contamination, the slides were autoclaved (glass) or sterilized in a 1% solution of bleach for 30 minutes and the petri dishes were sterilised by 30 minutes exposure to ultraviolet light. Overnight cultures of bacteria were diluted 1/1000 into 25 ml of fresh medium and grown for 24 hours, at 30° C. or 37° C. with 50 rpm shaking, allowing biofilm formation on the slides. After 24 h, the medium was replaced with fresh medium containing varying concentrations of SNP, SNAP, or GSNO (in addition to controls without NO generators) and the cells were incubated for a further 24 hours at the appropriate temperature with agitation at 50 rpm. The slides were then rinsed in sterile PBS to remove unattached or loosely attached cells.

The ability of SNP to increase the sensitivity of *V. cholerae* biofilms to antimicrobial treatments was also tested as described above, with the exception that, after the initial 24 hours of biofilm development, the NO donor was added in combination with the anti-microbial treatment. Controls included a no treatment control, and the antimicrobial alone and the cells were incubated for a further 24 hours at the appropriate temperature with agitation at 50 rpm. The slides were then rinsed in sterile PBS to remove unattached or loosely attached cells. All treatments were performed in triplicate.

Assessment of biofilm formation was performed by staining the cells with the BacLight Live-Dead Staining reagents (Molecular Probes Inc, USA) and subsequent confocal microscopy. Up to 15 randomly selected fields of view per slide were imaged in the x-y plane for subsequent image analysis. Image analysis was performed using the analysis package, ImageJ (http://rsb.info.nih.gov/ij) to determine total surface coverage. Results are presented as percentage cover of the total surface available per field of view.

Figure 10:
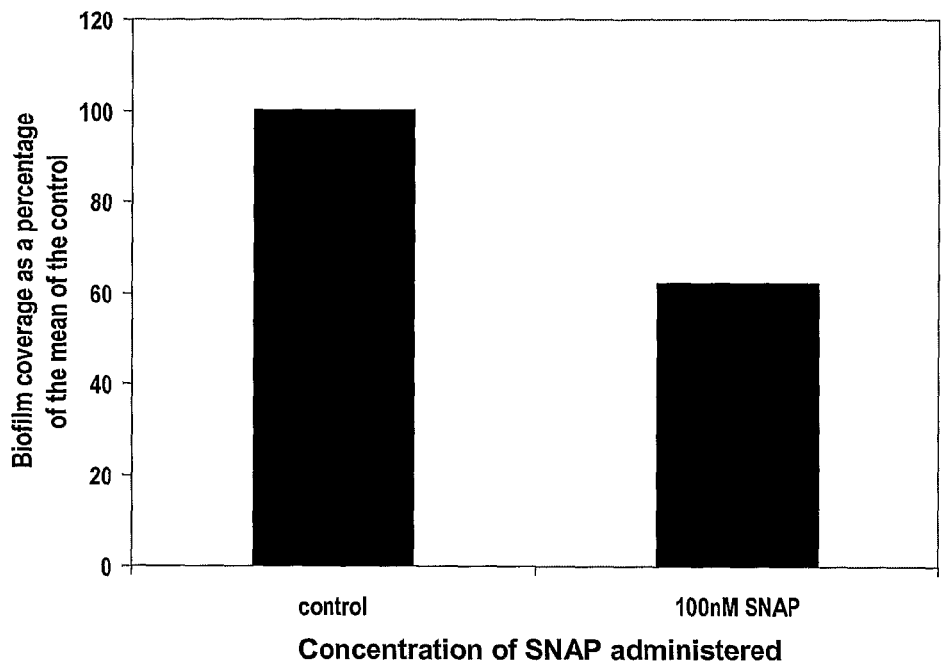
FIG. 10. Effect of SNP on dispersal of *Serratia marcescens* biofilms.
Figure 11:
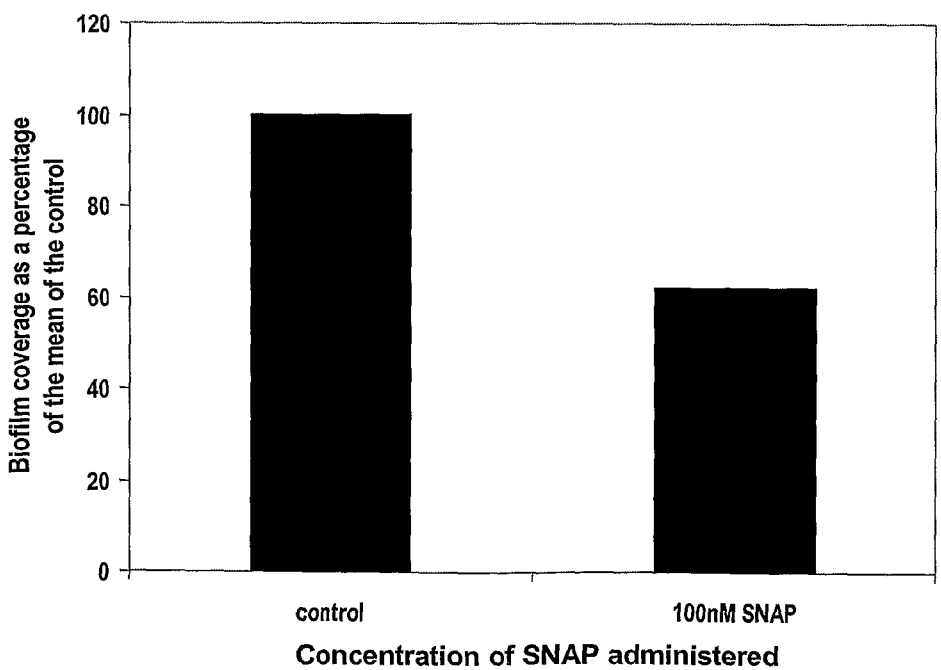
FIG. 11. Effect of SNAP on dispersal of *Serratia marcescens* biofilms.

FIG. 10 shows a concentration dependent dispersal of *S. marcescens* biofilms by SNP at concentrations between 0 and 500 nM, with more than 60% reduction in biofilm coverage at a concentration of 25 nM SNP. FIG. 11 shows that SNAP (100 nM) is also effective for dispersal of *S. marcescens* biofilms.

FIGS. 12 and 13 show similar results for the effects of SNP and SNAP on dispersal of *Vibrio cholerae* biofilms.

Figure 14:
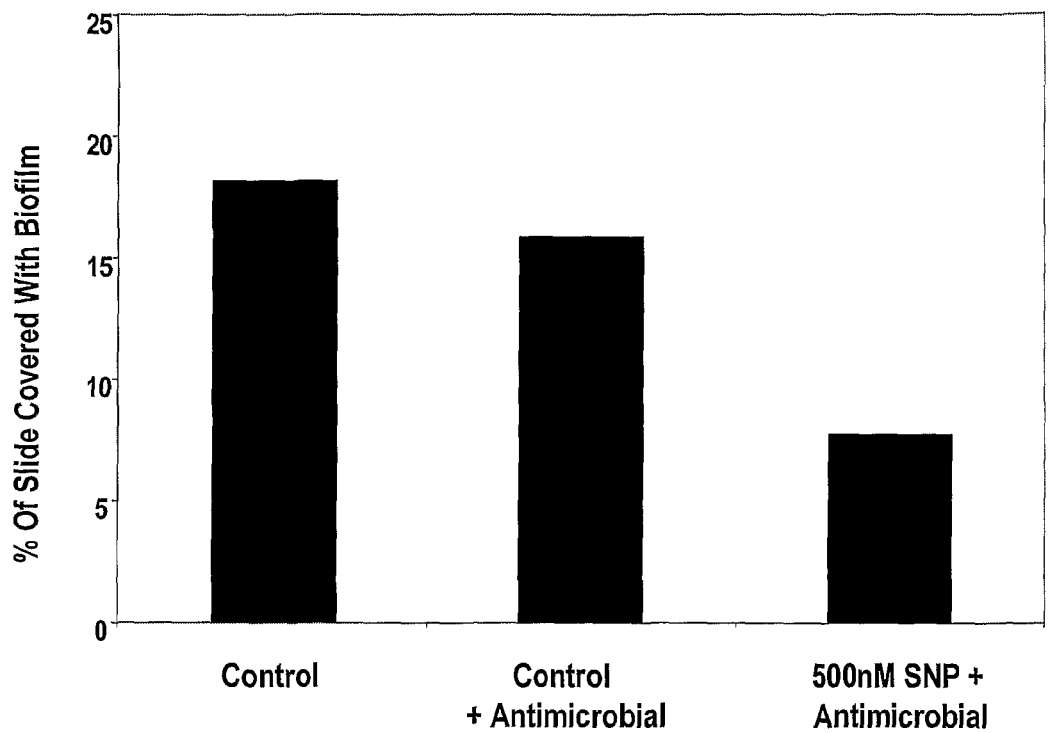
FIG. 14. Enhancement by SNP treatment of the antimicrobial activity of tetracycline (6 µg/mL) on biofilms of *Vibrio cholerae*.

FIG. 14 shows that SNP enhances the antimicrobial activity of tetracycline (6 µg/mL) on biofilms of *V. cholerae*. The concentration of tetracycline used was below the MIC for this organism.

Figure 15:
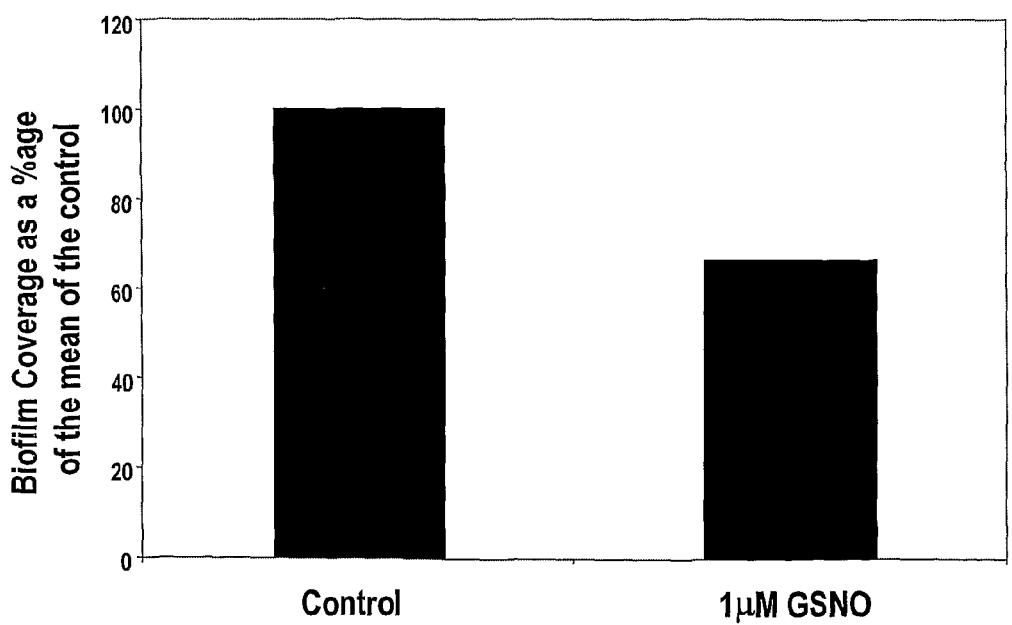
FIG. 15. Effect of GSNO on dispersal of *Vibrio cholerae* biofilms.
Figure 16:
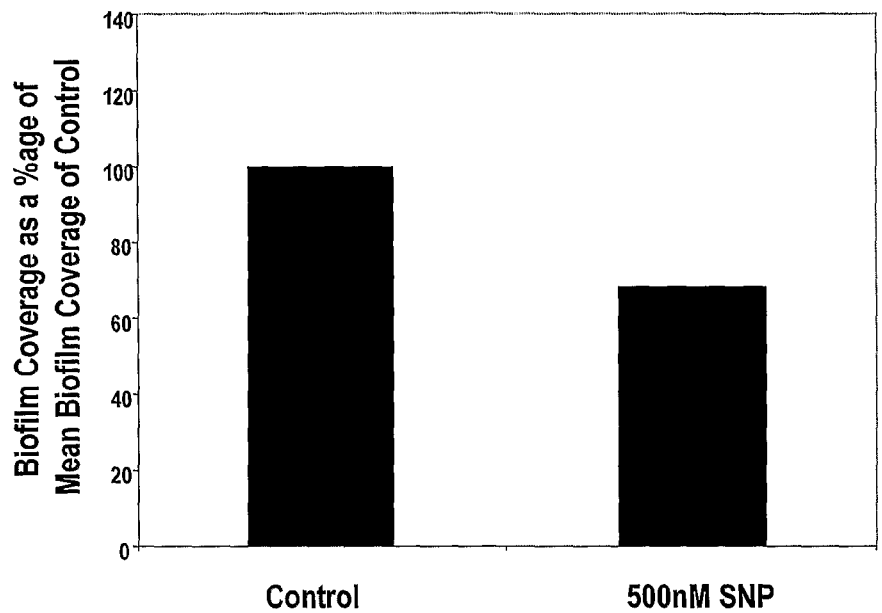
FIG. 16. Effect of SNP on dispersal of *E. coli* biofilms.

FIG. 15 shows that 1 µM GSNO has a significant effect on stability of *V. cholerae* biofilms, and FIG. 16 shows that 500 nM SNP has a significant effect on stability of *E. coli* biofilms.

Figure 17:
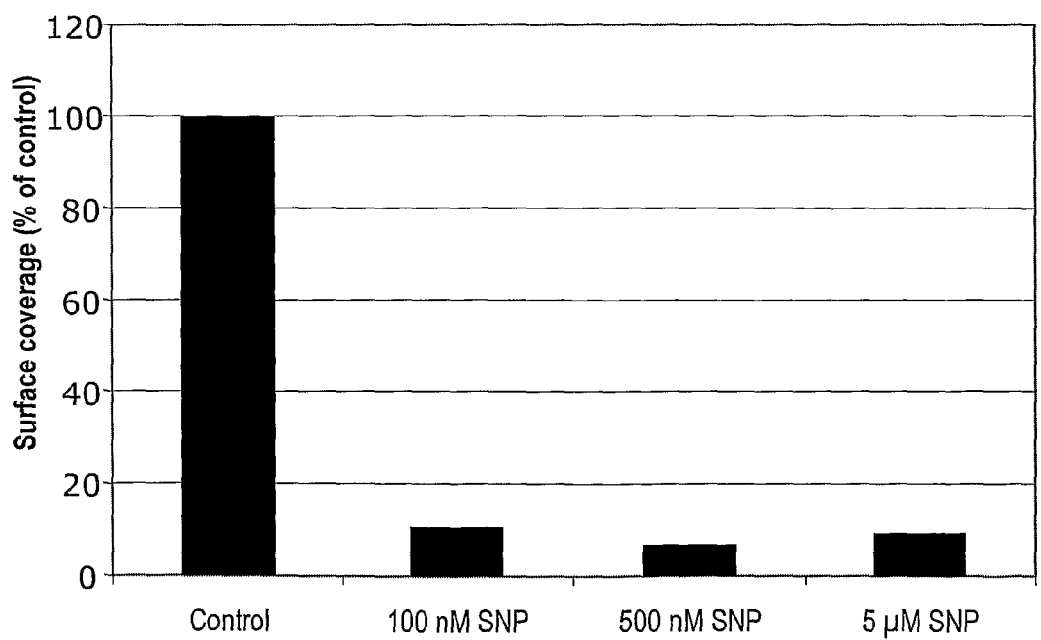
FIG. 17. Effect of SNP on dispersal of *Bacillus licheniformis* biofilms.

FIG. 17 shows a strong effect of SNP on stability of *Bacillus licheniformis* biofilms, with 100 nM SNP providing a 90% reduction in surface coverage by the biofilms.

Example 7

Low Levels of Nitric Oxide Induce Dispersal of *C. albicans* Biofilms

Cells were grown in 24 well polystyrene microtitre plates (Sarstedt) in Yeast peptone dextrose medium (YPD) at 30° C. with shaking at 100 rpm. Briefly, an overnight culture of *C. albicans* was diluted 1:100 into fresh medium and 1 ml inoculated into the wells. Biofilm was allowed to form for 24 hours, after which time the medium was replaced with fresh medium and SNP was added at concentrations of 0 nM, 25 nM, 100 nM, 500 nM, 1 µM and 5 µM. The cells were incubated a further 24 hours, at which time the wells were rinsed with PBS to remove loosely and unattached cells and stained with 1% crystal violet. The wells were washed thoroughly with PBS and the amount of crystal violet absorbed into the biofilm was measured using a Wallac-Victor$^2$ plate reader (Perkin-Elmer) at 540 nm.

Figure 18:
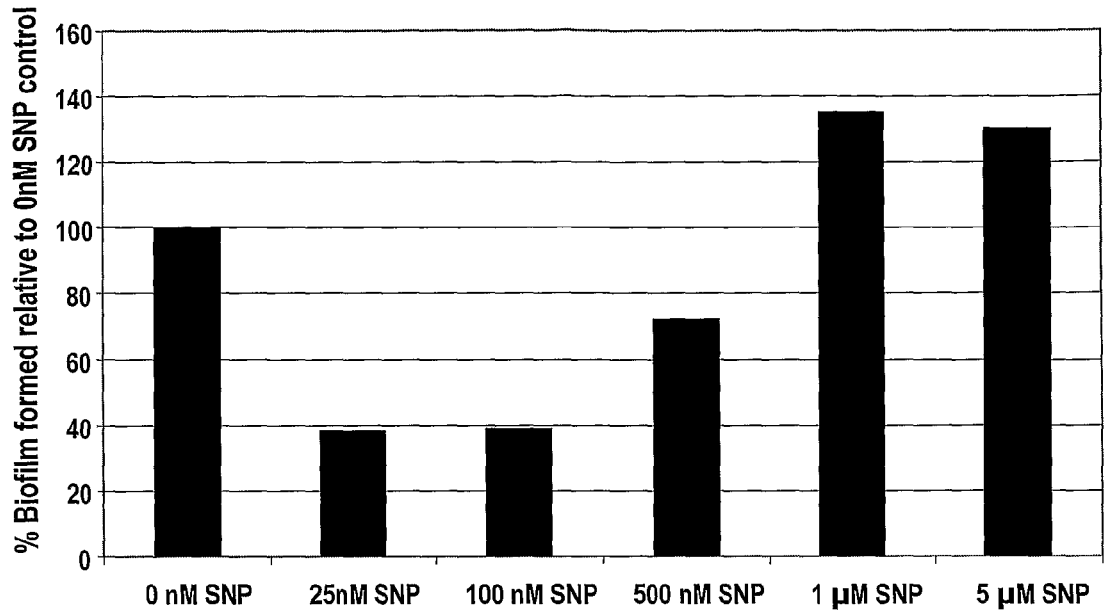
FIG. 18. Effect of SNP on dispersal of *Candida albicans* biofilms.

The results (FIG. 18) are presented as the percentage of the untreated control and show that SNP destabilises *C. albicans* biofilms at SNP concentrations below 1 µM, with more than 60% reduction in *C. albicans* biofilm in the 25 nM SNP treatment.

Example 8

Low Levels of Nitric Oxide Inhibit Formation of *S. epidermidis* Biofilms

Figure 19:
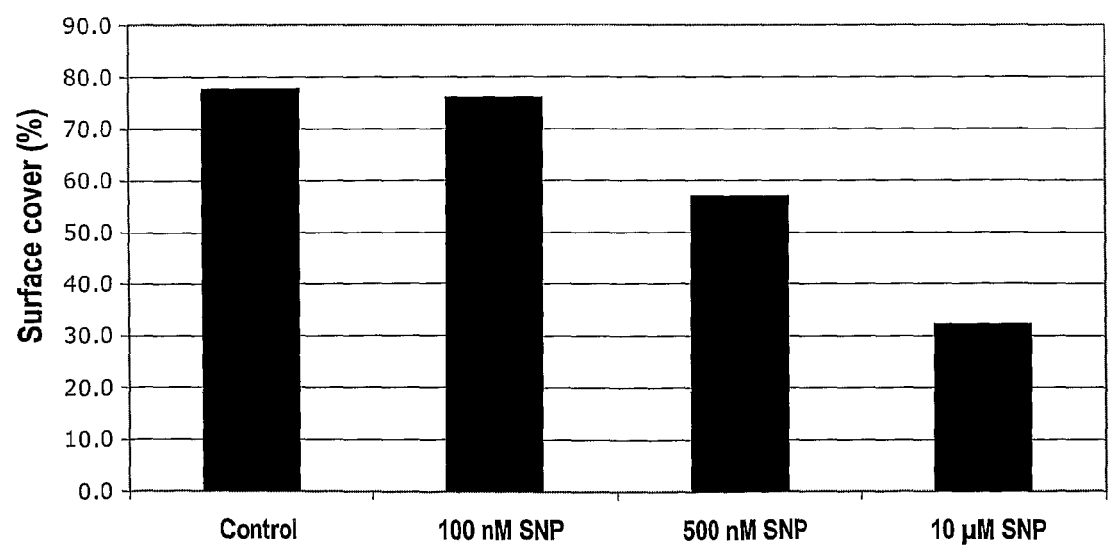
FIG. 19. Inhibition by SNP treatment of biofilm formation by *Staphylococcus epidermidis*.

The methods and materials used to test the effect of NO on biofilm formation and develop of *Staphylococcus epidermidis* were similar to those described above for *S. marcescens, V cholerae, E. coli* and *B. licheniformis*, using glass slides in petri dishes for cultivation of the biofilm. However, the NO donor, SNP, was added continuously to the cells, rather than after the initial 24 hours period of biofilm development. Results demonstrate that SNP addition can prevent the formation of a biofilm by *S. epidermidis* (FIG. 19) in a concentration-dependent manner.

Example 9

Low Levels of Nitric Oxide Induce Dispersal of *F. nucleatum* Biofilms

Figure 20:
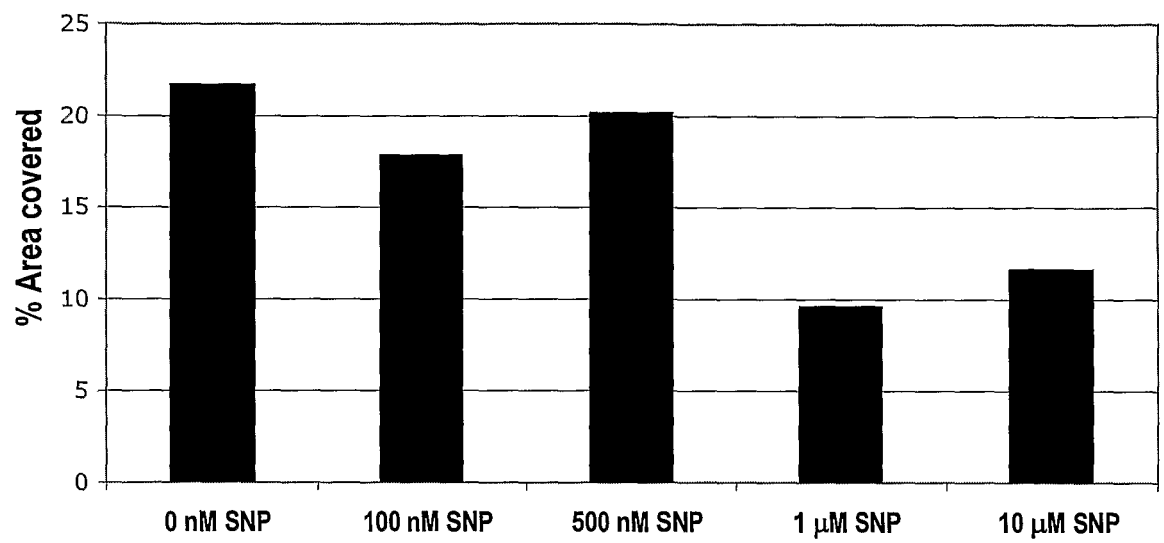
FIG. 20. Inhibition by SNP of attachment of *Fusobacterium nucleatum* to a glass surface.

To determine the potential effect of NO on anaerobic, oral bacteria, *Fusobacterium nucleatum* was selected as a model and key organism for biofilms of oral consortia. Briefly, an overnight culture was used to inoculate fresh medium (1:100). The cells were grown to an optical density (600 nm) of 0.1, at which time SNP was added to the cells to a concentration of 0 nM, 100 nM, 500 nM, 1 µM and 10 µM. A glass slide was also added to the tube of cells, and the bacteria were allowed to attach for 4 hours. At the end of the incubation period, the slides were removed, washed twice by dipping in sterile PBS to remove loosely associated cells, and stained with crystal violet, The attached cells were enumerated microscopically by digital image capture and subsequent image analysis. Results are presented as the percentage of cells attached in comparison to the control culture which was not exposed to SNP (FIG. 20), and show that addition of the NO generator, SNP, inhibits attachment of *F. nucleatum* to surfaces.

It will be appreciated that, although specific embodiments of the invention have been described herein for the purpose of illustration, various modifications may be made without deviating from the spirit and scope of the invention as defined in the following claims.

The claims defining the invention are as follows:

1. A method for promoting dispersal of a *Pseudomonas* or *Candida* microbial biofilm, the method comprising:
    adding to the environment of the *Pseudomonas* or *Candida* microbial biofilm an effective, non-toxic amount of nitric oxide or at least one nitric oxide generating or releasing agent; and
    inducing the accumulation of an effective amount of one or more reactive oxygen or nitrogen species within *Pseudomonas* or *Candida* microorganisms within the *Pseudomonas* or *Candida* microbial biofilm;
    wherein the effective, non-toxic amount of nitric oxide is equivalent to the amount of nitric oxide generated or released by about 25 nM to about 2.5 mM sodium nitroprusside for a *Pseudomonas* microbrial biofilm; and
    wherein the effective, non-toxic amount of nitric oxide is equivalent to the amount of nitric oxide generated or released by about 25 nM to about 100 nM sodium nitroprusside for a *Candida* microbrial biofilm.

2. The method of claim 1 wherein the at least one nitric oxide generating or releasing agent comprises one or more nitric oxide donors.

3. The method of claim 2 wherein the at least one nitric oxide donor is sodium nitroprusside, S-nitroso-L-glutathione, S-nitroso-N-acetylpenicillamine or a combination thereof.

4. The method of claim 1 wherein the microorganisms present in the biofilm or capable of forming a biofilm are of a single species selected from *Pseudomonas aeruginosa* or *Candida albicans*.

5. The method of claim 1 wherein the microorganisms present in the biofilm or capable of forming a biofilm are of multiple species.

6. The method of claim 1, wherein the microorganisms within said biofilm or capable of forming a biofilm comprise bacterial or fungal species.

7. The method of claim 1, further comprising treating said surface or medium with, incorporating in said surface or medium, or exposing the microorganisms within said biofilm or capable of forming a biofilm to, at least one antimicrobial agent.

8. The method of claim 7 wherein the antimicrobial agent is selected from an antibiotic, a surfactant, an oxidative stress-inducing agent, or a combination thereof.

9. The method of claim 1 wherein the one or more reactive oxygen or nitrogen species are selected from peroxynitrite, nitric oxide, hydrogen peroxide and superoxide radicals, or a combination thereof.

10. The method of claim 1 wherein said method comprises inducing differentiation events in microorganisms within said biofilm which lead to dispersal or wherein said method comprises preventing induction of differentiation events in microorganisms which lead to biofilm formation.

11. The method of claim 1 which comprises increasing the sensitivity of a microorganism to one or more antimicrobial agents.

12. The method of claim 1 comprising administering to a subject an effective amount of nitric oxide or at least one nitric oxide generating or releasing agent for the treatment of a biofilm-associated condition in said subject.

13. The method of claim 12 further comprising administering to said subject at least one antimicrobial agent.

14. The method of claim 4, wherein the microorganisms present in the biofilm or capable of forming a biofilm are *Pseudomonas aeruginosa*.

15. The method of claim 4, wherein the microorganisms present in the biofilm or capable of forming a biofilm are *Candida albicans*.

16. The method of claim 1, wherein the biofilm is a *Pseudomonas aeruginosa* biofilm and wherein about 25 nM to about 2.5 mM sodium nitroprusside is added to the environment of the biofilm.

17. The method of claim 1, wherein the biofilm is a *Candida albicans* biofilm and wherein about 25 nM to about 100 nM sodium nitroprusside is added to the environment of the biofilm.

* * * * *